United States Patent
Moeckel et al.

(10) Patent No.: US 6,783,967 B2
(45) Date of Patent: Aug. 31, 2004

(54) NUCLEOTIDE SEQUENCES WHICH CODE FOR THE RPOB GENE

(75) Inventors: Bettina Moeckel, Duesseldorf (DE); Brigitte Bathe, Salzkotten (DE); Thomas Hermann, Bielefeld (DE); Walter Pfefferle, Halle (DE); Michael Binder, Steinhagen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/887,052

(22) Filed: Jun. 25, 2001

(65) Prior Publication Data

US 2002/0119537 A1 Aug. 29, 2002

(30) Foreign Application Priority Data

Feb. 16, 2001 (DE) .......................................... 101 07 229

(51) Int. Cl.$^7$ .............................. C12N 9/12; C07H 21/04
(52) U.S. Cl. ....................... 435/194; 435/194; 435/183; 435/320.1; 435/252.3; 435/252.32; 536/23.1; 536/23.2; 536/23.7; 536/24.3
(58) Field of Search ................................. 435/194, 183, 435/320.1, 252.3, 252.32; 536/23.1, 23.2, 23.7, 24.3

(56) References Cited

FOREIGN PATENT DOCUMENTS

EP    1 108 790    6/2001

OTHER PUBLICATIONS

Imboden et all., The rpoB gene of *Mycobacterium tuberculosis*, Database EMBL on line, Accession No. U12205.1, Mar. 2000.*
Lubert Stryer, RNA Polymerase from *E. coli* is a Multisubunit Enzyme, Biochemistry, Third Edition, 1988, p. 70.
N. Honore, et al., Molecular Microbiology, vol. 7, No. 2, pp. 207–214, XP–000611934, "Nucleotide Sequence of the First Cosmid from the *Mycobacterium leprae* Genome Project: Structure and Function of the RIF–STR Regions", 1993.

* cited by examiner

*Primary Examiner*—Richard Hutson
(74) *Attorney, Agent, or Firm*—Oblon, Spivak, McClelland, Maier & Neustadt, P.C.

(57) ABSTRACT

The present invention relates to polynucleotides corresponding to the rpoB gene and which encode the β-subunit of RNA polymerase B, methods of producing L-amino acids, and methods of screening for polynucleotides which encode proteins having activity of the β-subunit of RNA polymerase B.

13 Claims, No Drawings

NUCLEOTIDE SEQUENCES WHICH CODE FOR THE RPOB GENE

CROSS-REFERENCE TO RELATED APPLICATION

The present application claims priority to German Application No. DE10107229.5 filed Feb. 16, 2001, the entire contents of which are incorporated herein by reference.

BACKGROUND OF THE INVENTION

1. Field of the Invention

The present invention relates to polynucleotides corresponding to the rpoB gene and which encode the β-subunit of RNA polymerase B, methods of producing L-amino acids, and methods of screening for polynucleotides which encode proteins having activity of the β-subunit of RNA polymerase B.

2. Discussion of the Background

L-amino acids, especially L-lysine, are used in human medicine and in the pharmaceuticals industry, in the foodstuffs industry and, very especially, in the feeding of animals.

It is known that amino acids are produced by fermentation of strains of coryneform bacteria, especially *Corynebacterium glutamicum*. Because of their great importance, attempts are continuously being made to improve the production processes. Improvements to the processes may concern measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites or are auxotrophic for metabolites that are important in terms of regulation, and which produce amino acids.

For a number of years, methods of recombinant DNA technology have also been used for improving the strain of L-amino acid-producing strains of Corynebacterium, by amplifying individual amino acid biosynthesis genes and studying the effect on amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that enhancement of the rpoB gene encoding the β-subunit of RNA polymerase B would improve L-amino acid yields.

SUMMARY OF THE INVENTION

One object of the present invention, is providing a new process adjuvant for improving the fermentative production of L-amino acids, particularly L-lysine and L-glutamate. Such process adjuvants include enhanced bacteria, preferably enhanced Coryneform bacteria which express enhanced levels of the β-subunit of RNA polymerase B which is encoded by the rpoB gene.

Thus, another object of the present invention is providing such a bacterium, which expresses enhanced amounts of the β-subunit of RNA polymerase B or gene products of the rpoB gene.

Another object of the present invention is providing a bacterium, preferably a Coryneform bacterium, which expresses a polypeptide that has an enhanced β-subunit of RNA polymerase B activity.

Another object of the invention is to provide a nucleotide sequence encoding a polypeptide which has a β-subunit of RNA polymerase B sequence. One embodiment of such a sequence is the nucleotide sequence of SEQ ID NO: 1. Other embodiments of such a sequence is the nucleotide sequences of SEQ ID NOS:3 and 5.

A further object of the invention is a method of making a β-subunit of RNA polymerase B or an isolated polypeptide having a β-subunit of RNA polymerase B activity, as well as use of such isolated polypeptides in the production of amino acids. One embodiment of such a polypeptide is the polypeptide having the amino acid sequence of SEQ ID NO: 2. Other embodiments of such a sequence is the amino acid sequence of SEQ ID NOS:4 and 6.

In one embodiment the invention provides isolated polypeptides comprising the amino acid sequences in SEQ ID NOS:2, 4 and/or 6.

Other objects of the invention include methods of detecting nucleic acid sequences homologous to SEQ ID NO: 1, particularly nucleic acid sequences encoding polypeptides that have the activity of a β-subunit of RNA polymerase B, and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is especially preferred.

Where L-lysine or lysine is mentioned hereinbelow, it is to be understood as meaning not only the bases but also the salts, such as, for example, lysine monohydrochloride or lysine sulfate.

The invention provides an isolated polynucleotide from coryneform bacteria, containing a polynucleotide sequence coding for the rpoB gene, selected from the group a) polynucleotide that is at least 70% identical with a polynucleotide that codes for a polypeptide containing the amino acid sequence of SEQ ID No. 2, b) polynucleotide that codes for a polypeptide containing an amino acid sequence that is at least 70% identical with the amino acid sequence of SEQ ID No. 2, c) polynucleotide that is complementary to the polynucleotides of a) or b), and d) polynucleotide containing at least 15 consecutive nucleotides of the polynucleotide sequence of a), b) or c), the polypeptide preferably exhibiting the activity of the β-subunit of RNA polymerase B.

The invention also provides the above-mentioned polynucleotide, it preferably being a replicatable DNA containing:

(i) the nucleotide sequence shown in SEQ ID No. 1, or (ii) at least one sequence that corresponds to sequence (i) within the region of the degeneracy of the genetic code, or (iii) at least one sequence that hybridizes with the sequence that is complementary to sequence (i) or (ii), and optionally (iv) sense mutations in (i) which are neutral in terms of function and which do not change the activity of the protein/polypeptide.

Finally, the invention also provides polynucleotides selected from the group a) polynucleotides containing at least 15 consecutive nucleotides selected from the nucleotide sequence of SEQ ID No. 1 between positions 1 and 701 b) polynucleotides containing at least 15 consecutive nucleotides selected from the nucleotide sequence of SEQ ID No. 1 between positions 702 and 4199 c) polynucleotides containing at least 15 consecutive nucleotides selected from the nucleotide sequence of SEQ ID No. 1 between positions 4200 and 5099.

The invention also provides a replicatable polynucleotide, especially DNA, containing the nucleotide sequence as shown in SEQ ID No. 1;

a polynucleotide that codes for a polypeptide containing the amino acid sequence as shown in SEQ ID No. 2;

a vector containing the polynucleotide of the invention, especially a shuttle vector or a plasmid vector, and coryneform bacteria which contain the vector or in which the rpoB gene has been enhanced.

The invention also provides polynucleotides consisting substantially of a polynucleotide sequence, which are obtainable by screening, by means of hybridization, a corresponding gene library of a coryneform bacteria that contains the complete gene or parts thereof, using a probe containing the sequence of the polynucleotide of the invention according to SEQ ID No. 1 or a fragment thereof, and isolating the mentioned polynucleotide sequence.

Polynucleotides that contain the sequences of the invention are suitable as hybridization probes for RNA, CDNA and DNA, in order to isolate in their complete length nucleic acids or polynucleotides or genes that code for the β-subunit of RNA polymerase B, or in order to isolate nucleic acids or polynucleotides or genes that are very similar to the sequence of the rpoB gene. They are likewise suitable for incorporation into so-called "arrays", "micro arrays" or "DNA chips" in order to detect and determine the corresponding polynucleotides.

Polynucleotides that contain the sequences of the invention are also suitable as primers, with the aid of which it is possible, by means of the polymerase chain reaction (PCR), to produce DNA of genes that code for the β-subunit of RNA polymerase B.

Such oligonucleotides acting as probes or primers contain at least 25, 26, 27, 28, 29 or 30, preferably at least 20, 21, 22, 23 or 24, very especially preferably at least 15, 16, 17, 18 or 19, consecutive nucleotides. Also suitable are oligonucleotides having a length of at least 31, 32, 33, 34, 35, 36, 37, 38, 39 or 40 or of at least 41, 42, 43, 44, 45, 46, 47, 48, 49 or 50 nucleotides. Oligonucleotides having a length of at least 100, 150, 200, 250 or 300 nucleotides may also be suitable.

"Isolated" means removed from its natural environment.

"Polynucleotide" generally refers to polyribonucleotides and polydeoxyribonucleotides, it being possible for the RNA or DNA to be unmodified or modified.

The polynucleotides of the invention include a polynucleotide according to SEQ ID No. 1 or a fragment prepared therefrom, and also polynucleotides that are at least especially from 70% to 80%, preferably at least from 81% to 85%, especially preferably at least from 86% to 90%, and very especially preferably at least 91%, 93%, 95%, 97% or 99%, identical with the polynucleotide according to SEQ ID No. 1, or with a fragment prepared therefrom.

"Polypeptides" are to be understood as being peptides or proteins that contain two or more amino acids bonded via peptide bonds.

The polypeptides of the invention include a polypeptide according to SEQ ID No. 2, especially those having the biological activity of the β-subunit of RNA polymerase B, and also those that are at least from 70% to 80%, preferably at least from 81% to 85%, especially preferably at least from 86% to 90%, and very especially preferably at least 91%, 93%, 95%, 97% or 99%, identical with the polypeptide according to SEQ ID No. 2 and exhibit the mentioned activity.

The invention also provides a process for the production, by fermentation, of amino acids selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using coryneform bacteria which, in particular, already produce amino acids and in which the nucleotide sequences coding for the rpoB gene are enhanced, especially overexpressed.

The term "enhancement" in this connection describes the increasing of the intracellular activity of one or more enzymes or proteins in a microorganism that are coded for by the corresponding DNA, by, for example, increasing the number of copies of the gene or genes, using a strong promoter or using a gene or allele that codes for a corresponding enzyme or protein having a high level of activity, and optionally by combining those measures.

The microorganisms provided by the present invention can produce L-amino acids from glucose, saccharose, lactose, fructose, maltose, molasses, starch, cellulose or from glycerol and ethanol. They may be representatives of coryneform bacteria, especially of the genus Corynebacterium. In the case of the genus Corynebacterium, special mention may be made of the species *Corynebacterium glutamicum,* which is known to those skilled in the art for its ability to produce L-amino acids.

Suitable strains of the genus Corynebacterium, especially of the species *Corynebacterium glutamicum* (*C. glutamicum*), are especially the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom, such as, for example, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM5714 and
*Corynebacterium glutamicum* DSM12866.

Preferably, a bacterial strain with attenuated expression of a rpoB gene that encodes a polypeptide with activity of the β-subunit of RNA polymerase B will improve amino acid yield at least 1%.

The inventors have succeeded in isolating the new rpoB gene of *C. glutamicum* which codes for the β-subunit of RNA polymerase B, which is a β-subunit of RNA polymerase B.

In order to isolate the rpoB gene or other genes from *C. glutamicum*, a gene library of that microorganism in *Escherichia coli* (*E. coli*) is first prepared. The preparation of gene libraries is written down in generally known textbooks and handbooks. There may be mentioned as an example the textbook of Winnacker: Gene und Klone, Eine Einführung in die Gentechnologie (Verlag Chemie, Weinheim, Germany, 1990) or the handbook of Sambrook et al.: Molecular Cloning, A Laboratory Manual (Cold Spring Harbor Laboratory Press, 1989). A very well known gene library is that of the *E. coli* K-12 strain W3110, which has been prepared by Kohara et al. (Cell 50, 495–508 (1987)) in λ-vectors. Bathe et al. (Molecular and General Genetics, 252:255–265, 1996) describe a gene library of *C. glutamicum* ATCC13032, which has been prepared with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (sic) (1992)) in turn describe a gene library of *C. glutamicum* ATCC13032 using the cosmid pHC79 (Hohn and Collins, Gene 11, 291–298 (1980)).

For the preparation of a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are especially those *E. coli* strains that are restriction- and recombination-defective. An example thereof is the strain DH5αmcr, which has been described by Grant et al. (Proceedings of the National Academy of Sciences USA, 87 (1990) 4645–4649). The long DNA fragments cloned with the aid of cosmids can then in turn be subcloned into customary vectors suitable for sequencing and then sequenced, as is described, for example, in Sanger et al. (Proceedings of the National Academy of Sciences of the United States of America, 74:5463–5467, 1977).

The resulting DNA sequences can then be studied using known algorithms or sequence-analysis programs, such as, for example, that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The novel DNA sequence of *C. glutamicum* coding for the rpoB gene has been found and, as SEQ ID No. 1, forms part of the present invention. Furthermore, the amino acid sequence of the corresponding protein has been derived from the present DNA sequence using the methods described above. The resulting amino acid sequence of the rpoB gene product is shown in SEQ ID No. 2. It is known that enzymes belonging to the host are able to cleave the N-terminal amino acid methionine or formylmethionine of the protein that is formed.

Coding DNA sequences that result from SEQ ID No. 1 by the degeneracy of the genetic code also form part of the invention. Likewise, DNA sequences that hybridize with SEQ ID No. 1 or parts of SEQ ID No. 1 form part of the invention. Furthermore, to those skilled in the art, conservative amino acid substitutions, such as, for example, the substitution of glycine with alanine or of aspartic acid with glutamic acid, in proteins are known as sense mutations, which do not lead to any fundamental change in the activity of the protein, that is to say are neutral in terms of function. Such mutations are known inter alia also as neutral substitutions. It is also known that changes at the N- and/or C-terminus of a protein do not substantially impair its function or may even stabilise it. The person skilled in the art will find relevant information inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences that result in a corresponding manner from SEQ ID No. 2 likewise form part of the invention.

Similarly, DNA sequences that hybridize with SEQ ID No. 1 or parts of SEQ ID No. 1 form part of the invention. Finally, DNA sequences that are produced by the polymerase chain reaction (PCR) using primers that result from SEQ ID No. 1 form part of the invention. Such oligonucleotides typically have a length of at least 15 nucleotides.

The person skilled in the art will find instructions on the identification of DNA sequences by means of hybridization inter alia in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say there are formed only hybrids in which the probe and the target sequence, i.e. the polynucleotides treated with the probe, are at least 70% identical. It is known that the stringency of the hybridization, including the washing steps, is influenced or determined by varying the buffer composition, the temperature and the salt concentration. The hybridization reaction is preferably carried out with relatively low stringency as compared with the washing steps (Hybaid Hybridisation Guide, Hybaid Limited, Teddington, UK, 1996).

There may be used for the hybridization reaction, for example, a 5×SSC buffer at a temperature of approximately from 50° C. to 68° C. In that case, probes may also hybridize with polynucleotides that are less than 70% identical with the sequence of the probe. Such hybrids are less stable and are removed by washing under stringent conditions. That may be achieved, for example, by lowering the salt concentration to 2×SSC and optionally subsequently to 0.5×SSC (The DIG System User's Guide for Filter Hybridisation, Boehringer Mannheim, Mannheim, Germany, 1995), a temperature of approximately from 50° C. to 68° C. being set. It is optionally possible to lower the salt concentration down to 0.1× SSC. By raising the hybridization temperature stepwise from 50° C. to 68° C. in steps of approximately from 1 to 2° C., it is possible to isolate polynucleotide fragments that are, for example, at least 70% or at least 80% or at least from 90% to 95% identical with the sequence of the probe used. Further instructions for hybridization are commercially available in the form of so-called kits (e.g. DIG Easy Hyb from Roche Diagnostics GmbH, Mannheim, Germany, Catalog No. 1603558).

The person skilled in the art will find instructions on the amplification of DNA sequences with the aid of the polymerase chain reaction (PCR) inter alia in the handbook of Gait: Oligonukleotide synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after enhancement of the rpoB gene.

In order to achieve overexpression, the number of copies of the corresponding genes can be increased, or the promoter and regulation region or the ribosome binding site, which is located upstream of the structural gene, can be mutated. Expression cassettes inserted upstream of the structural gene have a similar effect. By means of inducible promoters it is additionally possible to increase the expression in the course of the production of amino acids by fermentation. Expression is also improved by measures to prolong the life of the m-RNA. Furthermore, the enzyme activity is also enhanced by preventing degradation of the enzyme protein. The genes or gene constructs may either be present in plasmids with different numbers of copies or be integrated and amplified in the chromosome. Alternatively, overexpression of the genes in question may also be achieved by changing the composition of the medium and the manner in which culturing is carried out.

The person skilled in the art will find instructions thereon in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European patent specification 0 472 869, in U.S. Pat. No. 4,601,893, in Schwarzer and Puhler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in patent application WO 96/15246, in Malumbres et al. (Gene 134, 15–24 (1993)), in Japanese Offenlegungsschrift JP-A-10–229891, in Jensen and Hammer (Biotechnology and Bioengineering 58, 191–195 (1998)), in Makrides (Microbiological Reviews 60:512–538 (1996)) and in known textbooks of genetics and molecular biology.

For the purposes of enhancement, the rpoB gene of the invention was overexpressed, for example, with the aid of episomal plasmids. Suitable plasmids are those which are replicated in coryneform bacteria. Many known plasmid vectors, such as, for example, pZ1 (Menkel et al., Applied and Environmental Microbiology (1989) 64: 549–554), pEKEx1 (Eikmanns et al., Gene 102:93–98 (1991)) or pHS2–1 (Sonnen et al., Gene 107:69–74 (1991)), are based on the cryptic plasmids pHM1519, pBL1 or pGA1. Other plasmid vectors, such as, for example, those which are based on pCG4 (U.S. Pat. No. 4,489,160) or pNG2 (Serwold-Davis et al., FEMS Microbiology Letters 66, 119–124 (1990)) or pAG1 (U.S. Pat No. 5,158,891), may likewise be used.

Also suitable are those plasmid vectors with the aid of which the process of gene amplification by integration into the chromosome can be applied, as has been described, for example, by Reinscheid et al. (Applied and Environmental Microbiology 60, 126–132 (1994)) for the duplication or amplification of the hom-thrB operon. In that method, the complete gene is cloned into a plasmid vector that is able to replicate in a host (typically E. coli), but not in C. glutamicum. Suitable vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wisc., USA), pCR2.1-TOPO (Shuman (1994). Journal of Biological Chemistry 269:32678–32684; U.S. Pat. No. 5,487,993), pCR®Blunt (Invitrogen, Groningen, Netherlands; Bernard et al., Journal of Molecular Biology, 234: 534–541 (1993)), pEM1 (Schrumpf et al., 1991, Journal of Bacteriology 173:4510–4516) or pBGS8 (Spratt et al., 1986, Gene 41: 337–342). The plasmid vector containing the gene to be amplified is then transferred to the desired strain of C. glutamicum by conjugation or transformation. The method of conjugation is described, for example, in Schäfer et al. (Applied and Environmental Microbiology 60, 756–759 (1994)). Methods of transformation are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" occurrence, the resulting strain contains at least two copies of the gene in question.

It has also been found that the substitution of amino acids, especially in the sections between position 1 to 10, 190 to 200 and 420 to 450 in the amino acid sequence of the β-subunit of RNA polymerase B shown in SEQ ID No. 2, improves the lysine production of coryneform bacteria.

It has also been found that the substitution of amino acids at one or more positions selected from the group a) position 1 to 10, b) position 190 to 200 and c) position 420 to 450 in SEQ ID No. 2 may take place simultaneously.

In the region between position 1 to 10, preference is given to the substitution of L-proline at position 5 by L-leucine, L-isoleucine or L-valine.

In the region between position 190 to 200, preference is given to the substitution of L-serine at position 196 by L-phenylalanine or L-tyrosine.

In the region between 420 to 450, the following substitutions are preferred: substitution of L-leucine at position 424 by L-proline or L-arginine, substitution of L-serine at position 425 by L-threonine or L-alanine, substitution of L-glutamine at position 426 by L-leucine or L-lysine, substitution of L-aspartic acid at position 429 by L-isoleucine, L-valine or L-leucine, substitution of L-histidine at position 439 by any proteinogenic amino acid with the exception of L-histidine, is (sic) the substitution of L-serine at position 444 by L-leucine, L-tyrosine or L-tryptophan, and substitution of L-leucine at position 446 by L-proline or L-isoleucine.

Very special preference is given to one or more amino acid substitutions selected from the group: L-proline at position 5 by L-leucine, L-serine at position 196 by L-phenylalanine, L-aspartate at position 429 by L-valine, and L-histidine at position 439 by L-tyrosine.

SEQ ID No. 3 shows the base sequence of the allele rpoB-1547 contained in strain DM1547. The rpoB-1547 allele codes for a protein the amino acid sequence of which is shown in SEQ ID No. 4. The protein contains L-leucine at position 5, L-phenylalanine at position 196 and L-valine at position 429. The DNA sequence of the rpoB-1547 allele (SEQ ID No. 3) contains the following base substitutions as compared with the rpoB wild-type gene (SEQ ID No. 1): thymine at position 715 instead of cytosine, thymine at position 1288 instead of cytosine, and thymine at position 1987 instead of adenine.

SEQ ID No. 5 shows the base sequence of the allele rpoB-1546 contained in strain DM1546. The rpoB-1546 allele codes for a protein the amino acid sequence of which is shown in SEQ ID No. 6. The protein contains L-tyrosine at position 439. The DNA sequence of the rpoB-1546 allele (SEQ ID No. 5) contains the following base substitutions as compared with the rpoB wild-type gene (SEQ ID No. 1): thymine at position 2016 instead of cytosine.

There may be employed for the mutagenesis conventional methods of mutagenesis using mutagenic substances such as, for example, N-methyl-N'-nitro-N-nitrosoguanidine or ultraviolet light. There may also be used for the mutagenesis in vitro methods such as, for example, treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR), as is described in the handbook of Newton and Graham (PCR, Spektrum Akademischer Verlag, Heidelberg, 1994).

In addition, it may be advantageous for the production of L-amino acids to enhance, especially to overexpress, in addition to the rpoB gene, one or more enzymes of the biosynthesis pathway in question, of glycolysis, of the anaplerotic pathway, of the citric acid cycle, of the pentose phosphate cycle, of amino acid export, and, optionally, regulatory proteins.

Accordingly, for the production of L-lysine, in addition to enhancing the rpoB gene, one or more genes selected from the group the gene dapA coding for dihydrodipicolinate synthase (EP-B 0 197 335), the gene gap coding for glyceraldehyde 3-phosphate dehydrogenase (Eikmanns (1992), Journal of Bacteriology 174:6076–6086), the gene tpi coding for triose phosphate isomerase (Eikmanns (1992), Journal of Bacteriology 174:6076–6086), the gene pgk coding for 3-phosphoglycerate kinase (Eikmanns (1992), Journal of Bacteriology 174:6076–6086), the gene zwf coding for glucose-6-phosphate dehydrogenase (JP-A-09224661), the gene pyc coding for pyruvate carboxylase (DE-A-198 31 609), the gene mqo coding for malate quinone oxidoreductase (Molenaar et al., European Journal of Biochemistry 254, 395–403 (1998)), the gene lysC coding for a feed-back resistant aspartate kinase (Kalinowski et al., Molecular Microbiologie 5(5), 1197–1204 (1991)), the gene lysE coding for lysine export (DE-A-195 48 222), the gene zwa1 coding for the Zwa1 protein (DE: 19959328.0, DSM 13115), and the rpsL gene coding for ribosomal protein S12 and shown in SEQ ID No. 7 and 8 may be enhanced, especially overexpressed.

The term "attenuation" in this connection describes the diminution or exclusion of the intracellular activity of one or more enzymes (proteins) in a microorganism that are coded for by the corresponding DNA, by, for example, using a weak promoter or using a gene or allele that codes for a corresponding enzyme having low activity, or by inactivating the corresponding gene or enzyme (protein), and optionally by combining those measures.

Furthermore, it may be advantageous for the production of L-amino acids, in addition to enhancing the rpoB gene, to attenuate, especially to diminish the expression of, one or more genes selected from the group the gene pck coding for phosphoenol pyruvate carboxykinase (DE 199 50 409.1; DSM 13047), the gene pgi coding for glucose-6-phosphate isomerase (U.S. Ser. No. 09/396,478; DSM 12969), the gene poxB coding for pyruvate oxidase (DE: 1995 1975.7; DSM 13114), the gene zwa2 coding for the Zwa2 protein (DE: 19959327.2, DSM 13113).

It may also be advantageous for the production of amino acids, in addition to enhancing the rpoB gene, to exclude undesired secondary reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms produced according to the invention also form part of the invention and can be cultivated, for the purposes of the production of amino acids, continuously or discontinuously in the batch, fed batch or repeated fed batch process. A summary of known cultivation methods is described in the textbook of Chmiel (Bioprozeßtechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Braunschweig/Wiesbaden, 1994)).

The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981).

There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be fed in in a suitable manner during the cultivation.

In order to control the pH value of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours.

Methods of determining L-amino acids are known from the prior art. The analysis may be carried out, for example, as described in Spackman et al. (Analytical Chemistry, 30, (1958), 1190) by ion-exchange chromatography with subsequent ninhydrin derivatization, or it may be carried out by reversed phase HPLC, as described in Lindroth et al. (Analytical Chemistry (1979) 51: 1167–1174).

Pure cultures of the following microorganisms were deposited on Jan. 16, 2001 at the Deutsche Sammlung für Mikroorganismen und Zellkulturen (DSMZ, Braunschweig, Germany) in accordance with the Budapest Treaty:

Corynebacterium glutamicum strain DM1546 as DSM 13993

Corynebacterium glutamicum strain DM1547 as DSM 13994.

The process of the invention is used for the production of amino acids by fermentation.

The present invention is explained in greater detail below by means of Examples.

The isolation of plasmid DNA from *Escherichia coli* and all techniques for restriction, Klenow and alkaline phosphatase treatment were carried out according to Sambrook et al. (Molecular Cloning. A Laboratory Manual (1989) Cold Spring Harbour Laboratory Press, Cold Spring Harbor, N.Y., USA). Methods for the transformation of *Escherichia coli* are also described in that handbook.

The composition of common nutrient media, such as LB or TY medium, will also be found in the handbook of Sambrook et al.

EXAMPLE 1

Preparation of a genomic cosmid gene library from *Corynebacterium glutamicum* ATCC 13032

Chromosomal DNA from *Corynebacterium glutamicum* ATCC 13032 is isolated as described in Tauch et al. (1995, Plasmid 33:168–179) and partially cleaved with the restriction enzyme Sau3AI (Amersham Pharmacia, Freiburg, Germany, product description Sau3AI, Code no. 27-0913-02). The DNA fragments are dephosphorylated with shrimp alkaline phosphatase (Roche Diagnostics GmbH, Mannheim, Germany, product description SAP, Code no. 1758250). The DNA of cosmid vector SuperCosi (Wahl et al. (1987) Proceedings of the National Academy of Sciences USA 84:2160–2164), obtained from Stratagene (La Jolla, USA, product description SuperCos1 Cosmid Vektor Kit, Code no. 251301), is cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA is then cleaved with the restriction enzyme BamHI (Amersham Pharmacia, Freiburg, Germany, product description BamHI, Code no. 27-0868-04). The cosmid DNA so treated is mixed with the treated ATCC13032 DNA, and the batch is treated with T4-DNA ligase (Amersham Pharmacia, Freiburg, Germany, product description T4-DNA ligase, Code no. 27-0870-04). The ligation mixture is then packed in phages with the aid of Gigapack II XL Packing Extract (Stratagene, La Jolla, USA, product description Gigapack II XL Packing Extract, Code no. 200217).

For infection of *E. coli* strain NM554 (Raleigh et al. 1988, Nucleic Acid Research 16:1563–1575), the cells are taken up in 10 mM $MgSO_4$ and mixed with an aliquot of the phage suspension. Infection and titration of the cosmid library are carried out as described in Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones are selected.

EXAMPLE 2

Isolation and sequencing of the rpoB gene

The cosmid DNA of an individual colony is isolated using the Qiaprep Spin Miniprep Kit (Product No. 27106, Qiagen, Hilden, Germany) according to the manufacturer's instructions, and partially cleaved with the restriction enzyme Sau3AI (Amersham Pharmacia, Freiburg, Germany, product description Sau3AI, Product No. 27-0913-02). The DNA fragments are dephosphorylated with shrimp alkaline phosphatase (Roche Diagnostics GmbH, Mannheim, Germany, product description SAP, Product No. 1758250). After separation by gel electrophoresis, cosmid fragments having a size in the range from 1500 to 2000 bp are isolated using the QiaExII Gel Extraction Kit (Product No. 20021, Qiagen, Hilden, Germany).

The DNA of sequencing vector pZero-1, obtained from Invitrogen (Groningen, Netherlands, product description Zero Background Cloning Kit, Product No. K2500-01), is cleaved with the restriction enzyme BamHI (Amersham Pharmacia, Freiburg, Germany, product description BamHI, Product No. 27-0868-04). Ligation of the cosmid fragments into the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). The ligation mixture is then electroporated into *E. coli* strain DH5αMCR (Grant, 1990, Proceedings of the National Academy of Sciences U.S.A., 87:4645–4649) (Tauch et al. 1994, FEMS Microbiol Letters, 123:343–347) and plated out on LB agar (Lennox, 1955, Virology, 1:190) with 50 mg/l Zeocin.

Plasmid preparation of the recombinant clones is carried out using the Biorobot 9600 (Product No. 900200, Qiagen, Hilden, Germany). Sequencing is effected by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) is used. Separation by gel electrophoresis and analysis of the sequencing reaction is carried out in a "Rotiphorese NF Acrylamid/Bisacrylamid" gel (29:1) (Product No. A124.1, Roth, Karlsruhe, Germany) using the "ABI Prism 377" sequencing device from PE Applied Biosystems (Weiterstadt, Germany).

The resulting crude sequence data are then processed using the Staden program package (1986, Nucleic Acids Research, 14:217–231) Version 97-0. The individual sequences of the pZero1 derivatives are assembled to a coherent contig. The computer-assisted coding region analysis is prepared using the program XNIP (Staden, 1986, Nucleic Acids Research, 14:217–231).

The resulting nucleotide sequence is shown in SEQ ID No. 1. Analysis of the nucleotide sequence gives an open reading frame of 3497 base pairs, which is designated the rpoB gene. The rpoB gene codes for a protein of 1165 amino acids.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide which encodes a protein comprising the amino acid sequence of SEQ ID NO:2.

2. An isolated polynucleotide which comprises SEQ ID NO: 1.

3. An isolated polynucleotide which is complementary to the polynucleotide of claim 2.

4. A vector comprising the isolated polynucleotide of claim 1.

5. A vector comprising the isolated polynucleotide of claim 2.

6. A host cell comprising the isolated polynucleotide of claim 1.

7. A host cell comprising the isolated polynucleotide of claim 2.

8. The host cell of claim 6, which is a Coryneform bacterium.

9. The host cell of claim 7, which is a Coryneform bacterium.

10. The host cell of claim 6, wherein said host cell is selected from the group consisting of Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum, and Brevibacterium divaricatum.

11. The host cell of claim 7, wherein said host cell is selected from the group consisting of Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum, and Brevibacterium divaricatum.

12. A method for making a β-subunit of RNA polymerase B, comprising:

culturing the host cell of claim 6 for a time and under conditions suitable for expression of the β-subunit of RNA polymerase B, and collecting the β-subunit of RNA polymerase B.

13. A method for making a β-subunit of RNA polymerase B, comprising:

culturing the host cell of claim 7 for a time and under conditions suitable for expression of the β-subunit of RNA polymerase B, and collecting the β-subunit of RNA polymerase B.

* * * * *

SEQUENCE LISTING

<160> NUMBER OF SEQ ID NOS: 8

<210> SEQ ID NO 1
<211> LENGTH: 5099
<212> TYPE: DNA
<213> ORGANISM: Corynebacterium glutamicum
<220> FEATURE:
<221> NAME/KEY: CDS
<222> LOCATION: (702)..(4196)

<400> SEQUENCE: 1

```
acaatgtgac tcgtgatttt tgggtggatc agcgtaccgg tttggttgtc gatctagctg     60
aaaatattga tgatttttac ggcgaccgca gcggccagaa gtacgaacag aaattgcttt    120
tcgacgcctc cctcgacgat gcagctgtct ctaagctggt tgcacaggcc gaaagcatcc    180
ctgatggaga tgtgagcaaa atcgcaaata ccgtaggtat tgtgatcggt gcggtattgg    240
ctctcgtggg cctggccggg tgttttgggg cgtttgggaa gaaacgtcga gaagcttaac    300
ctgctgttca aatagatttt ccctgtttcg aattgcggaa accccgggtt tgtttgctag    360
ggtgcctcgt agaagggtc aagaagattt ctgggaaacg cgcccgtgcg gttggttgct    420
aatagcacgc ggagcaccag atgaaaaatc tcccctttac tttcgcgcgc gattggtata    480
ctctgagtcg ttgcgttgga attcgtgact cttttctgtt cctgtagcgc caagaccttg    540
atcaaggtgg tttaaaaaaa ccgatttgac aaggtcattc agtgctatct ggagtcgttc    600 aggggatcg ggttcctcag cagaccaatt gctcaaaaat accagcggtg ttgatctgca    660
cttaatggcc ttgaccagcc aggtgcaatt acccgcgtga g gtg ctg gaa gga ccc    716
                                              Val Leu Glu Gly Pro
                                                1               5 atc ttg gca gtc tcc cgc cag acc aag tca gtc gtc gat att ccc ggt     764
Ile Leu Ala Val Ser Arg Gln Thr Lys Ser Val Val Asp Ile Pro Gly
        10                  15                  20 gca ccg cag cgt tat tct ttc gcg aag gtg tcc gca ccc att gag gtg     812
Ala Pro Gln Arg Tyr Ser Phe Ala Lys Val Ser Ala Pro Ile Glu Val
    25                  30                  35 ccc ggg cta cta gat ctt caa ctg gat tct tac tcc tgg ctg att ggt     860
Pro Gly Leu Leu Asp Leu Gln Leu Asp Ser Tyr Ser Trp Leu Ile Gly
    40                  45                  50 acg cct gag tgg cgt gct cgt cag aag gaa gaa ttc ggc gag gga gcc     908
Thr Pro Glu Trp Arg Ala Arg Gln Lys Glu Glu Phe Gly Glu Gly Ala
55                  60                  65
```

-continued

| | |
|---|---|
| cgc gta acc agc ggc ctt gag aac att ctc gag gag ctc tcc cca atc<br>Arg Val Thr Ser Gly Leu Glu Asn Ile Leu Glu Glu Leu Ser Pro Ile<br>70                     75                          80                        85 | 956 |
| cag gat tac tct gga aac atg tcc ctg agc ctt tcg gag cca cgc ttc<br>Gln Asp Tyr Ser Gly Asn Met Ser Leu Ser Leu Ser Glu Pro Arg Phe<br>                          90                          95                        100 | 1004 |
| gaa gac gtc aag aac acc att gac gag gcg aaa gaa aag gac atc aac<br>Glu Asp Val Lys Asn Thr Ile Asp Glu Ala Lys Glu Lys Asp Ile Asn<br>                   105                     110                    115 | 1052 |
| tac gcg gcg cca ctg tat gtg acc gcg gag ttc gtc aac aac acc acc<br>Tyr Ala Ala Pro Leu Tyr Val Thr Ala Glu Phe Val Asn Asn Thr Thr<br>120                     125                     130 | 1100 |
| ggt gaa atc aag tct cag act gtc ttc atc ggc gat ttc cca atg atg<br>Gly Glu Ile Lys Ser Gln Thr Val Phe Ile Gly Asp Phe Pro Met Met<br>135                     140                     145 | 1148 |
| acg gac aag gga acg ttc atc atc aac gga acc gaa cgc gtt gtg gtc<br>Thr Asp Lys Gly Thr Phe Ile Ile Asn Gly Thr Glu Arg Val Val Val<br>150                     155                     160                    165 | 1196 |
| agc cag ctc gtc cgc tcc ccg ggc gtg tac ttt gac cag acc atc gat<br>Ser Gln Leu Val Arg Ser Pro Gly Val Tyr Phe Asp Gln Thr Ile Asp<br>                   170                     175                    180 | 1244 |
| aag tca act gag cgt cca ctg cac gcc gtg aag gtt att cct tcc cgt<br>Lys Ser Thr Glu Arg Pro Leu His Ala Val Lys Val Ile Pro Ser Arg<br>185                     190                     195 | 1292 |
| ggt gct tgg ctt gag ttt gac gtc gat aag cgc gat tcg gtt ggt gtt<br>Gly Ala Trp Leu Glu Phe Asp Val Asp Lys Arg Asp Ser Val Gly Val<br>                   200                     205                    210 | 1340 |
| cgt att gac cgc aag cgt cgc cag cca gtc acc gta ctg ctg aag gct<br>Arg Ile Asp Arg Lys Arg Arg Gln Pro Val Thr Val Leu Leu Lys Ala<br>215                     220                     225 | 1388 |
| ctt ggc tgg acc act gag cag atc acc gag cgt ttc ggt ttc tct gaa<br>Leu Gly Trp Thr Thr Glu Gln Ile Thr Glu Arg Phe Gly Phe Ser Glu<br>230                     235                     240                    245 | 1436 |
| atc atg atg tcc acc ctc gag tcc gat ggt gta gca aac acc gat gag<br>Ile Met Met Ser Thr Leu Glu Ser Asp Gly Val Ala Asn Thr Asp Glu<br>                   250                     255                    260 | 1484 |
| gca ttg ctg gag atc tac cgc aag cag cgt cca ggc gag cag cct acc<br>Ala Leu Leu Glu Ile Tyr Arg Lys Gln Arg Pro Gly Glu Gln Pro Thr<br>265                     270                     275 | 1532 |
| cgc gac ctt gcg cag tcc ctc ctg gac aac agc ttc ttc cgt gca aag<br>Arg Asp Leu Ala Gln Ser Leu Leu Asp Asn Ser Phe Phe Arg Ala Lys<br>                   280                     285                    290 | 1580 |
| cgc tac gac ctg gct cgc gtt ggt cgt tac aag atc aac cgc aag ctc<br>Arg Tyr Asp Leu Ala Arg Val Gly Arg Tyr Lys Ile Asn Arg Lys Leu<br>295                     300                     305 | 1628 |
| ggc ctt ggt ggc gac cac gat ggt ttg atg act ctt act gaa gag gac<br>Gly Leu Gly Gly Asp His Asp Gly Leu Met Thr Leu Thr Glu Glu Asp<br>310                     315                     320                    325 | 1676 |
| atc gca acc acc atc gag tac ctg gtg cgt ctg cac gca ggt gag cgc<br>Ile Ala Thr Thr Ile Glu Tyr Leu Val Arg Leu His Ala Gly Glu Arg<br>                   330                     335                    340 | 1724 |
| gtc atg act tct cca aat ggt gaa gag atc cca gtc gag acc gat gac<br>Val Met Thr Ser Pro Asn Gly Glu Glu Ile Pro Val Glu Thr Asp Asp<br>345                     350                     355 | 1772 |
| atc gac cac ttt ggt aac cgt cgt ctg cgt acc gtt ggc gaa ctg atc<br>Ile Asp His Phe Gly Asn Arg Arg Leu Arg Thr Val Gly Glu Leu Ile<br>                   360                     365                    370 | 1820 |
| cag aac cag gtc cgt gtc ggc ctg tcc cgc atg gag cgc gtt gtt cgt<br>Gln Asn Gln Val Arg Val Gly Leu Ser Arg Met Glu Arg Val Val Arg | 1868 |

-continued

|  |  |  |
|---|---|---|
| 375 | 380 | 385 | gag cgt atg acc acc cag gat gcg gag tcc att act cct act tcc ttg    1916
Glu Arg Met Thr Thr Gln Asp Ala Glu Ser Ile Thr Pro Thr Ser Leu
390             395             400             405 atc aac gtt cgt cct gtc tct gca gct atc cgt gag ttc ttc gga act    1964
Ile Asn Val Arg Pro Val Ser Ala Ala Ile Arg Glu Phe Phe Gly Thr
            410             415             420 tcc cag ctg tct cag ttc atg gac cag aac aac tcc ctg tct ggt ttg    2012
Ser Gln Leu Ser Gln Phe Met Asp Gln Asn Asn Ser Leu Ser Gly Leu
        425             430             435 act cac aag cgt cgt ctg tcg gct ctg ggc ccg ggt ggt ctg tcc cgt    2060
Thr His Lys Arg Arg Leu Ser Ala Leu Gly Pro Gly Gly Leu Ser Arg
    440             445             450 gag cgc gcc ggc atc gag gtt cga gac gtt cac cca tct cac tac ggc    2108
Glu Arg Ala Gly Ile Glu Val Arg Asp Val His Pro Ser His Tyr Gly
455             460             465 cgt atg tgc cca att gag act ccg gaa ggt cca aac att ggc ctg atc    2156
Arg Met Cys Pro Ile Glu Thr Pro Glu Gly Pro Asn Ile Gly Leu Ile
470             475             480             485 ggt tcc ttg gct tcc tat gct cga gtg aac cca ttc ggt ttc att gag    2204
Gly Ser Leu Ala Ser Tyr Ala Arg Val Asn Pro Phe Gly Phe Ile Glu
            490             495             500 acc cca tac cgt cgc atc atc gac ggc aag ctg acc gac cag att gac    2252
Thr Pro Tyr Arg Arg Ile Ile Asp Gly Lys Leu Thr Asp Gln Ile Asp
        505             510             515 tac ctt acc gct gat gag gaa gac cgc ttc gtt gtt gcg cag gca aac    2300
Tyr Leu Thr Ala Asp Glu Glu Asp Arg Phe Val Val Ala Gln Ala Asn
    520             525             530 acg cac tac gac gaa gag ggc aac atc acc gat gag acc gtc act gtt    2348
Thr His Tyr Asp Glu Glu Gly Asn Ile Thr Asp Glu Thr Val Thr Val
535             540             545 cgt ctg aag gac ggc gac atc gcc atg gtt ggc cgc aac gcg gtt gat    2396
Arg Leu Lys Asp Gly Asp Ile Ala Met Val Gly Arg Asn Ala Val Asp
550             555             560             565 tac atg gac gtt tcc cct cgt cag atg gtt tct gtt ggt acc gcg atg    2444
Tyr Met Asp Val Ser Pro Arg Gln Met Val Ser Val Gly Thr Ala Met
            570             575             580 att cca ttc ctg gag cac gac gat gct aac cgt gca ctg atg ggc gcg    2492
Ile Pro Phe Leu Glu His Asp Asp Ala Asn Arg Ala Leu Met Gly Ala
        585             590             595 aac atg cag aag cag gct gtg cca ctg att cgt gcc gag gct cct ttc    2540
Asn Met Gln Lys Gln Ala Val Pro Leu Ile Arg Ala Glu Ala Pro Phe
    600             605             610 gtg ggc acc ggt atg gag cag cgc gca gca tac gac gcc ggc gac ctg    2588
Val Gly Thr Gly Met Glu Gln Arg Ala Ala Tyr Asp Ala Gly Asp Leu
615             620             625 gtt att acc cca gtc gca ggt gtg gaa aac gtt tca gct gac ttc        2636
Val Ile Thr Pro Val Ala Gly Val Val Glu Asn Val Ser Ala Asp Phe
630             635             640             645 atc acc atc atg gct gat gac ggc aag cgc gaa acc tac ctg ctg cgt    2684
Ile Thr Ile Met Ala Asp Asp Gly Lys Arg Glu Thr Tyr Leu Leu Arg
            650             655             660 aag ttc cag cgc acc aac cag ggc acc agc tac aac cag aag cct ttg    2732
Lys Phe Gln Arg Thr Asn Gln Gly Thr Ser Tyr Asn Gln Lys Pro Leu
        665             670             675 gtt aac ttg ggc gag cgc gtt gaa gct ggc cag gtt att gct gat ggt    2780
Val Asn Leu Gly Glu Arg Val Glu Ala Gly Gln Val Ile Ala Asp Gly
    680             685             690 cca ggt acc ttc aat ggt gaa atg tcc ctt ggc cgt aac ctt ctg gtt    2828

-continued

| | | |
|---|---|---|
| Pro Gly Thr Phe Asn Gly Glu Met Ser Leu Gly Arg Asn Leu Leu Val<br>695           700           705 | | |
| gcg ttc atg cct tgg gaa ggc cac aac tac gag gat gcg atc atc ctc<br>Ala Phe Met Pro Trp Glu Gly His Asn Tyr Glu Asp Ala Ile Ile Leu<br>710           715           720           725 | 2876 | |
| aac cag aac atc gtt gag cag gac atc ttg acc tcg atc cac atc gag<br>Asn Gln Asn Ile Val Glu Gln Asp Ile Leu Thr Ser Ile His Ile Glu<br>730           735           740 | 2924 | |
| gag cac gag atc gat gcc cgc gac act aag ctt ggc gcc gaa gaa atc<br>Glu His Glu Ile Asp Ala Arg Asp Thr Lys Leu Gly Ala Glu Glu Ile<br>745           750           755 | 2972 | |
| acc cgc gac atc cct aat gtg tct gaa gaa gtc ctc aag gac ctc gac<br>Thr Arg Asp Ile Pro Asn Val Ser Glu Glu Val Leu Lys Asp Leu Asp<br>760           765           770 | 3020 | |
| gac cgc ggt att gtc cgc atc ggt gct gat gtt cgt gac ggc gac atc<br>Asp Arg Gly Ile Val Arg Ile Gly Ala Asp Val Arg Asp Gly Asp Ile<br>775           780           785 | 3068 | |
| ctg gtc ggt aag gtc acc cct aag ggc gag acc gag ctc acc ccg gaa<br>Leu Val Gly Lys Val Thr Pro Lys Gly Glu Thr Glu Leu Thr Pro Glu<br>790           795           800           805 | 3116 | |
| gag cgc ttg ctg cgc gca atc ttc ggt gag aag gcc cgc gaa gtt cgc<br>Glu Arg Leu Leu Arg Ala Ile Phe Gly Glu Lys Ala Arg Glu Val Arg<br>810           815           820 | 3164 | |
| gat acc tcc atg aag gtg cct cac ggt gag acc ggc aag gtc atc ggc<br>Asp Thr Ser Met Lys Val Pro His Gly Glu Thr Gly Lys Val Ile Gly<br>825           830           835 | 3212 | |
| gtg cgt cac ttc tcc cgc gag gac gac gac gat ctg gct cct ggc gtc<br>Val Arg His Phe Ser Arg Glu Asp Asp Asp Asp Leu Ala Pro Gly Val<br>840           845           850 | 3260 | |
| aac gag atg atc cgt atc tac gtt gct cag aag cgt aag atc cag gac<br>Asn Glu Met Ile Arg Ile Tyr Val Ala Gln Lys Arg Lys Ile Gln Asp<br>855           860           865 | 3308 | |
| ggc gat aag ctc gct ggc cgc cac ggt aac aag ggt gtt gtc ggt aaa<br>Gly Asp Lys Leu Ala Gly Arg His Gly Asn Lys Gly Val Val Gly Lys<br>870           875           880           885 | 3356 | |
| att ttg cct cag gaa gat atg cca ttc ctt cca gac ggc act cct gtt<br>Ile Leu Pro Gln Glu Asp Met Pro Phe Leu Pro Asp Gly Thr Pro Val<br>890           895           900 | 3404 | |
| gac atc atc ttg aac acc cac ggt gtt cca cgt cgt atg aac att ggt<br>Asp Ile Ile Leu Asn Thr His Gly Val Pro Arg Arg Met Asn Ile Gly<br>905           910           915 | 3452 | |
| cag gtt ctt gag acc cac ctt ggc tgg ctg gca tct gct ggt tgg tcc<br>Gln Val Leu Glu Thr His Leu Gly Trp Leu Ala Ser Ala Gly Trp Ser<br>920           925           930 | 3500 | |
| gtg gat cct gaa gat cct gag aac gct gag ctc gtc aag act ctg cct<br>Val Asp Pro Glu Asp Pro Glu Asn Ala Glu Leu Val Lys Thr Leu Pro<br>935           940           945 | 3548 | |
| gca gac ctc ctc gag gtt cct gct ggt tcc ttg act gca act cct gtg<br>Ala Asp Leu Leu Glu Val Pro Ala Gly Ser Leu Thr Ala Thr Pro Val<br>950           955           960           965 | 3596 | |
| ttc gac ggt gcg tca aac gaa gag ctc gca ggc ctg ctc gct aat tca<br>Phe Asp Gly Ala Ser Asn Glu Glu Leu Ala Gly Leu Leu Ala Asn Ser<br>970           975           980 | 3644 | |
| cgt cca aac cgc gac ggc gac gtc atg gtt aac gcg gat ggt aaa gca<br>Arg Pro Asn Arg Asp Gly Asp Val Met Val Asn Ala Asp Gly Lys Ala<br>985           990           995 | 3692 | |
| acg ctt atc gac ggt cgc tcc ggt gag cct tac ccg tac ccg gtt<br>Thr Leu Ile Asp Gly Arg Ser Gly Glu Pro Tyr Pro Tyr Pro Val<br>1000          1005          1010 | 3737 | |

```
                                                          -continued tcc atc ggc tac atg tac atg ctg aag ctg cac cac ctc gtt gac          3782
Ser Ile Gly Tyr Met Tyr Met Leu Lys Leu His His Leu Val Asp
        1015                1020                1025 gag aag atc cac gca cgt tcc act ggt cct tac tcc atg att acc          3827
Glu Lys Ile His Ala Arg Ser Thr Gly Pro Tyr Ser Met Ile Thr
    1030                1035                1040 cag cag cca ctg ggt ggt aaa gca cag ttc ggt gga cag cgt ttc          3872
Gln Gln Pro Leu Gly Gly Lys Ala Gln Phe Gly Gly Gln Arg Phe
1045                1050                1055 ggc gaa atg gag gtg tgg gca atg cag gca tac ggc gct gcc tac          3917
Gly Glu Met Glu Val Trp Ala Met Gln Ala Tyr Gly Ala Ala Tyr
        1060                1065                1070 aca ctt cag gag ctg ctg acc atc aag tct gat gac gtg gtt ggc          3962
Thr Leu Gln Glu Leu Leu Thr Ile Lys Ser Asp Asp Val Val Gly
    1075                1080                1085 cgt gtc aag gtc tac gaa gca att gtg aag ggc gag aac atc ccg          4007
Arg Val Lys Val Tyr Glu Ala Ile Val Lys Gly Glu Asn Ile Pro
1090                1095                1100 gat cca ggt att cct gag tcc ttc aag gtt ctc ctc aag gag ctc          4052
Asp Pro Gly Ile Pro Glu Ser Phe Lys Val Leu Leu Lys Glu Leu
        1105                1110                1115 cag tcc ttg tgc ctg aac gtg gag gtt ctc tcc gca gac ggc act          4097
Gln Ser Leu Cys Leu Asn Val Glu Val Leu Ser Ala Asp Gly Thr
    1120                1125                1130 cca atg gag ctc gcg ggt gac gac gac gac ttc gat cag gca ggc          4142
Pro Met Glu Leu Ala Gly Asp Asp Asp Asp Phe Asp Gln Ala Gly
1135                1140                1145 gcc tca ctt ggc atc aac ctg tcc cgt gac gag cgt tcc gac gcc          4187
Ala Ser Leu Gly Ile Asn Leu Ser Arg Asp Glu Arg Ser Asp Ala
        1150                1155                1160 gac acc gca tagcagatca gaaaacaacc gctagaaatc aagccataca              4236
Asp Thr Ala
    1165 tcccccggac attgaagaga tgttctgggg ggaaagggag ttttacgtgc tcgacgtaaa    4296 cgtcttcgat gagctccgca tcggcctggc caccgccgac gacatccgcc gttggtccaa    4356 gggtgaggtc aagaagccgg agaccatcaa ctaccgaacc ctcaagcctg agaaggacgg    4416 tctgttctgc gagcgtatct tcggtccaac tcgcgactgg gagtgcgcct gcggtaagta    4476 caagcgtgtc cgctacaagg gcatcatctg tgaacgctgt ggcgttgagg tcaccaagtc    4536 caaggtgcgc cgtgagcgca tgggacacat tgagctcgct gcaccagtaa cccacatttg    4596 gtacttcaag ggcgttccat cacgcctcgg ctaccttttg gaccttgctc caaaggacct    4656 ggacctcatc atctacttcg gtgcgaacat catcaccagc gtggacgaag aggctcgcca    4716 cagcgaccag accactcttg aggcagaaat gcttctggag aagaaggacg ttgaggcaga    4776 cgcagagtct gacattgctg agcgtgctga aaagctcgaa gaggatcttg ctgaacttga    4836 ggcagctggc gctaaggccg acgctcgccc caaggttcag gctgctgccg ataaggaaat    4896 gcagcacatc cgtgagcgtg cacagcgcga atcgatcgt ctcgatgagg tctggcagac     4956 cttcatcaag cttgctccaa agcagatgat ccgcgatgag aagctctacg atgaactgat    5016 cgaccgctac gaggattact tcaccggtgg tatgggtgca gagtccattg aggctttgat    5076 ccagaacttc gaccttgatg ctg                                            5099

<210> SEQ ID NO 2
<211> LENGTH: 1165
<212> TYPE: PRT
<213> ORGANISM: Corynebacterium glutamicum
```

<400> SEQUENCE: 2

```
Val Leu Glu Gly Pro Ile Leu Ala Val Ser Arg Gln Thr Lys Ser Val
1               5                   10                  15
Val Asp Ile Pro Gly Ala Pro Gln Arg Tyr Ser Phe Ala Lys Val Ser
            20                  25                  30
Ala Pro Ile Glu Val Pro Gly Leu Leu Asp Leu Gln Leu Asp Ser Tyr
        35                  40                  45
Ser Trp Leu Ile Gly Thr Pro Glu Trp Arg Ala Arg Gln Lys Glu Glu
    50                  55                  60
Phe Gly Glu Gly Ala Arg Val Thr Ser Gly Leu Glu Asn Ile Leu Glu
65                  70                  75                  80
Glu Leu Ser Pro Ile Gln Asp Tyr Ser Gly Asn Met Ser Leu Ser Leu
                85                  90                  95
Ser Glu Pro Arg Phe Glu Asp Val Lys Asn Thr Ile Asp Glu Ala Lys
            100                 105                 110
Glu Lys Asp Ile Asn Tyr Ala Ala Pro Leu Tyr Val Thr Ala Glu Phe
        115                 120                 125
Val Asn Asn Thr Thr Gly Glu Ile Lys Ser Gln Thr Val Phe Ile Gly
    130                 135                 140
Asp Phe Pro Met Met Thr Asp Lys Gly Thr Phe Ile Ile Asn Gly Thr
145                 150                 155                 160
Glu Arg Val Val Val Ser Gln Leu Val Arg Ser Pro Gly Val Tyr Phe
                165                 170                 175
Asp Gln Thr Ile Asp Lys Ser Thr Glu Arg Pro Leu His Ala Val Lys
            180                 185                 190
Val Ile Pro Ser Arg Gly Ala Trp Leu Glu Phe Asp Val Asp Lys Arg
        195                 200                 205
Asp Ser Val Gly Val Arg Ile Asp Arg Lys Arg Arg Gln Pro Val Thr
    210                 215                 220
Val Leu Leu Lys Ala Leu Gly Trp Thr Thr Glu Gln Ile Thr Glu Arg
225                 230                 235                 240
Phe Gly Phe Ser Glu Ile Met Met Ser Thr Leu Glu Ser Asp Gly Val
                245                 250                 255
Ala Asn Thr Asp Glu Ala Leu Leu Glu Ile Tyr Arg Lys Gln Arg Pro
            260                 265                 270
Gly Glu Gln Pro Thr Arg Asp Leu Ala Gln Ser Leu Leu Asp Asn Ser
        275                 280                 285
Phe Phe Arg Ala Lys Arg Tyr Asp Leu Ala Arg Val Gly Arg Tyr Lys
    290                 295                 300
Ile Asn Arg Lys Leu Gly Leu Gly Gly Asp His Asp Gly Leu Met Thr
305                 310                 315                 320
Leu Thr Glu Glu Asp Ile Ala Thr Thr Ile Glu Tyr Leu Val Arg Leu
                325                 330                 335
His Ala Gly Glu Arg Val Met Thr Ser Pro Asn Gly Glu Glu Ile Pro
            340                 345                 350
Val Glu Thr Asp Asp Ile Asp His Phe Gly Asn Arg Arg Leu Arg Thr
        355                 360                 365
Val Gly Glu Leu Ile Gln Asn Gln Val Arg Val Gly Leu Ser Arg Met
    370                 375                 380
Glu Arg Val Val Arg Glu Arg Met Thr Thr Gln Asp Ala Glu Ser Ile
385                 390                 395                 400
Thr Pro Thr Ser Leu Ile Asn Val Arg Pro Val Ser Ala Ala Ile Arg
```

-continued

```
                        405                 410                 415
Glu Phe Phe Gly Thr Ser Gln Leu Ser Gln Phe Met Asp Gln Asn Asn
            420                 425                 430
Ser Leu Ser Gly Leu Thr His Lys Arg Arg Leu Ser Ala Leu Gly Pro
        435                 440                 445
Gly Gly Leu Ser Arg Glu Arg Ala Gly Ile Glu Val Arg Asp Val His
    450                 455                 460
Pro Ser His Tyr Gly Arg Met Cys Pro Ile Glu Thr Pro Glu Gly Pro
465                 470                 475                 480
Asn Ile Gly Leu Ile Gly Ser Leu Ala Ser Tyr Ala Arg Val Asn Pro
                485                 490                 495
Phe Gly Phe Ile Glu Thr Pro Tyr Arg Arg Ile Ile Asp Gly Lys Leu
            500                 505                 510
Thr Asp Gln Ile Asp Tyr Leu Thr Ala Asp Glu Glu Asp Arg Phe Val
        515                 520                 525
Val Ala Gln Ala Asn Thr His Tyr Asp Glu Glu Gly Asn Ile Thr Asp
    530                 535                 540
Glu Thr Val Thr Val Arg Leu Lys Asp Gly Asp Ile Ala Met Val Gly
545                 550                 555                 560
Arg Asn Ala Val Asp Tyr Met Asp Val Ser Pro Arg Gln Met Val Ser
                565                 570                 575
Val Gly Thr Ala Met Ile Pro Phe Leu Glu His Asp Asp Ala Asn Arg
            580                 585                 590
Ala Leu Met Gly Ala Asn Met Gln Lys Gln Ala Val Pro Leu Ile Arg
        595                 600                 605
Ala Glu Ala Pro Phe Val Gly Thr Gly Met Glu Gln Arg Ala Ala Tyr
    610                 615                 620
Asp Ala Gly Asp Leu Val Ile Thr Pro Val Ala Gly Val Val Glu Asn
625                 630                 635                 640
Val Ser Ala Asp Phe Ile Thr Ile Met Ala Asp Asp Gly Lys Arg Glu
                645                 650                 655
Thr Tyr Leu Leu Arg Lys Phe Gln Arg Thr Asn Gln Gly Thr Ser Tyr
            660                 665                 670
Asn Gln Lys Pro Leu Val Asn Leu Gly Glu Arg Val Glu Ala Gly Gln
        675                 680                 685
Val Ile Ala Asp Gly Pro Gly Thr Phe Asn Gly Glu Met Ser Leu Gly
    690                 695                 700
Arg Asn Leu Leu Val Ala Phe Met Pro Trp Glu Gly His Asn Tyr Glu
705                 710                 715                 720
Asp Ala Ile Ile Leu Asn Gln Asn Ile Val Glu Gln Asp Ile Leu Thr
                725                 730                 735
Ser Ile His Ile Glu Glu His Glu Ile Asp Ala Arg Asp Thr Lys Leu
            740                 745                 750
Gly Ala Glu Glu Ile Thr Arg Asp Ile Pro Asn Val Ser Glu Glu Val
        755                 760                 765
Leu Lys Asp Leu Asp Asp Arg Gly Ile Val Arg Ile Gly Ala Asp Val
    770                 775                 780
Arg Asp Gly Asp Ile Leu Val Gly Lys Val Thr Pro Lys Gly Glu Thr
785                 790                 795                 800
Glu Leu Thr Pro Glu Glu Arg Leu Leu Arg Ala Ile Phe Gly Glu Lys
                805                 810                 815
Ala Arg Glu Val Arg Asp Thr Ser Met Lys Val Pro His Gly Glu Thr
            820                 825                 830
```

```
Gly Lys Val Ile Gly Val Arg His Phe Ser Arg Glu Asp Asp Asp
        835                 840                 845
Leu Ala Pro Gly Val Asn Glu Met Ile Arg Ile Tyr Val Ala Gln Lys
    850                 855                 860
Arg Lys Ile Gln Asp Gly Asp Lys Leu Ala Gly Arg His Gly Asn Lys
865                 870                 875                 880
Gly Val Val Gly Lys Ile Leu Pro Gln Glu Asp Met Pro Phe Leu Pro
                885                 890                 895
Asp Gly Thr Pro Val Asp Ile Ile Leu Asn Thr His Gly Val Pro Arg
            900                 905                 910
Arg Met Asn Ile Gly Gln Val Leu Glu Thr His Leu Gly Trp Leu Ala
        915                 920                 925
Ser Ala Gly Trp Ser Val Asp Pro Glu Asp Pro Glu Asn Ala Glu Leu
    930                 935                 940
Val Lys Thr Leu Pro Ala Asp Leu Leu Glu Val Pro Ala Gly Ser Leu
945                 950                 955                 960
Thr Ala Thr Pro Val Phe Asp Gly Ala Ser Asn Glu Glu Leu Ala Gly
                965                 970                 975
Leu Leu Ala Asn Ser Arg Pro Asn Arg Asp Gly Asp Val Met Val Asn
            980                 985                 990
Ala Asp Gly Lys Ala Thr Leu Ile Asp Gly Arg Ser Gly Glu Pro Tyr
        995                 1000                1005
Pro Tyr Pro Val Ser Ile Gly Tyr Met Tyr Met Leu Lys Leu His
    1010                1015                1020
His Leu Val Asp Glu Lys Ile His Ala Arg Ser Thr Gly Pro Tyr
    1025                1030                1035
Ser Met Ile Thr Gln Gln Pro Leu Gly Gly Lys Ala Gln Phe Gly
    1040                1045                1050
Gly Gln Arg Phe Gly Glu Met Glu Val Trp Ala Met Gln Ala Tyr
    1055                1060                1065
Gly Ala Ala Tyr Thr Leu Gln Glu Leu Leu Thr Ile Lys Ser Asp
    1070                1075                1080
Asp Val Val Gly Arg Val Lys Val Tyr Glu Ala Ile Val Lys Gly
    1085                1090                1095
Glu Asn Ile Pro Asp Pro Gly Ile Pro Glu Ser Phe Lys Val Leu
    1100                1105                1110
Leu Lys Glu Leu Gln Ser Leu Cys Leu Asn Val Glu Val Leu Ser
    1115                1120                1125
Ala Asp Gly Thr Pro Met Glu Leu Ala Gly Asp Asp Asp Phe
    1130                1135                1140
Asp Gln Ala Gly Ala Ser Leu Gly Ile Asn Leu Ser Arg Asp Glu
    1145                1150                1155
Arg Ser Asp Ala Asp Thr Ala
    1160                1165

<210> SEQ ID NO 3
<211> LENGTH: 5099
<212> TYPE: DNA
<213> ORGANISM: Corynebacterium glutamicum
<220> FEATURE:
<221> NAME/KEY: CDS
<222> LOCATION: (702)..(4196)

<400> SEQUENCE: 3
acaatgtgac tcgtgatttt tgggtggatc agcgtaccgg tttggttgtc gatctagctg    60
```

```
aaaatattga tgatttttac ggcgaccgca gcggccagaa gtacgaacag aaattgcttt    120
tcgacgcctc cctcgacgat gcagctgtct ctaagctggt tgcacaggcc gaaagcatcc    180
ctgatggaga tgtgagcaaa atcgcaaata ccgtaggtat tgtgatcggt gcggtattgg    240
ctctcgtggg cctggccggg tgttttgggg cgtttgggaa gaaacgtcga gaagcttaac    300
ctgctgttca aatagatttt ccctgtttcg aattgcggaa accccgggtt tgtttgctag    360
ggtgcctcgt agaagggtc aagaagattt ctgggaaacg cgcccgtgcg gttggttgct    420
aatagcacgc ggagcaccag atgaaaaatc tcccctttac tttcgcgcgc gattggtata    480
ctctgagtcg ttgcgttgga attcgtgact cttttttcgtt cctgtagcgc caagaccttg    540
atcaaggtgg tttaaaaaaa ccgatttgac aaggtcattc agtgctatct ggagtcgttc    600
agggggatcg ggttcctcag cagaccaatt gctcaaaaat accagcggtg ttgatctgca    660
cttaatggcc ttgaccagcc aggtgcaatt acccgcgtga g gtg ctg gaa gga ctc    716
                                             Val Leu Glu Gly Leu
                                              1               5 atc ttg gca gtc tcc cgc cag acc aag tca gtc gtc gat att ccc ggt    764
Ile Leu Ala Val Ser Arg Gln Thr Lys Ser Val Val Asp Ile Pro Gly
             10                  15                  20 gca ccg cag cgt tat tct ttc gcg aag gtg tcc gca ccc att gag gtg    812
Ala Pro Gln Arg Tyr Ser Phe Ala Lys Val Ser Ala Pro Ile Glu Val
         25                  30                  35 ccc ggg cta cta gat ctt caa ctg gat tct tac tcc tgg ctg att ggt    860
Pro Gly Leu Leu Asp Leu Gln Leu Asp Ser Tyr Ser Trp Leu Ile Gly
     40                  45                  50 acg cct gag tgg cgt gct cgt cag aag gaa gaa ttc ggc gag gga gcc    908
Thr Pro Glu Trp Arg Ala Arg Gln Lys Glu Glu Phe Gly Glu Gly Ala
 55                  60                  65 cgc gta acc agc ggc ctt gag aac att ctc gag gag ctc tcc cca atc    956
Arg Val Thr Ser Gly Leu Glu Asn Ile Leu Glu Glu Leu Ser Pro Ile
 70              75                  80                  85 cag gat tac tct gga aac atg tcc ctg agc ctt tcg gag cca cgc ttc   1004
Gln Asp Tyr Ser Gly Asn Met Ser Leu Ser Leu Ser Glu Pro Arg Phe
                 90                  95                 100 gaa gac gtc aag aac acc att gac gag gcg aaa gaa aag gac atc aac   1052
Glu Asp Val Lys Asn Thr Ile Asp Glu Ala Lys Glu Lys Asp Ile Asn
             105                 110                 115 tac gcg gcg cca ctg tat gtg acc gcg gag ttc gtc aac aac acc acc   1100
Tyr Ala Ala Pro Leu Tyr Val Thr Ala Glu Phe Val Asn Asn Thr Thr
         120                 125                 130 ggt gaa atc aag tct cag act gtc ttc atc ggc gat ttc cca atg atg   1148
Gly Glu Ile Lys Ser Gln Thr Val Phe Ile Gly Asp Phe Pro Met Met
 135                 140                 145 acg gac aag gga acg ttc atc atc aac gga acc gaa cgc gtt gtg gtc   1196
Thr Asp Lys Gly Thr Phe Ile Ile Asn Gly Thr Glu Arg Val Val Val
150                 155                 160                 165 agc cag ctc gtc cgc tcc ccg ggc gtg tac ttt gac cag acc atc gat   1244
Ser Gln Leu Val Arg Ser Pro Gly Val Tyr Phe Asp Gln Thr Ile Asp
                 170                 175                 180 aag tca act gag cgt cca ctg cac gcc gtg aag gtt att cct ttc cgt   1292
Lys Ser Thr Glu Arg Pro Leu His Ala Val Lys Val Ile Pro Phe Arg
             185                 190                 195 ggt gct tgg ctt gag ttt gac gtc gat aag cgc gat tcg gtt ggt gtt   1340
Gly Ala Trp Leu Glu Phe Asp Val Asp Lys Arg Asp Ser Val Gly Val
         200                 205                 210 cgt att gac cgc aag cgt cgc cag cca gtc acc gta ctg ctg aag gct   1388
Arg Ile Asp Arg Lys Arg Arg Gln Pro Val Thr Val Leu Leu Lys Ala
```

-continued

```
              215                 220                 225
ctt ggc tgg acc act gag cag atc acc gag cgt ttc ggt ttc tct gaa    1436
Leu Gly Trp Thr Thr Glu Gln Ile Thr Glu Arg Phe Gly Phe Ser Glu
230                 235                 240                 245 atc atg atg tcc acc ctc gag tcc gat ggt gta gca aac acc gat gag    1484
Ile Met Met Ser Thr Leu Glu Ser Asp Gly Val Ala Asn Thr Asp Glu
                250                 255                 260 gca ttg ctg gag atc tac cgc aag cag cgt cca ggc gag cag cct acc    1532
Ala Leu Leu Glu Ile Tyr Arg Lys Gln Arg Pro Gly Glu Gln Pro Thr
            265                 270                 275 cgc gac ctt gcg cag tcc ctc ctg gac aac agc ttc ttc cgt gca aag    1580
Arg Asp Leu Ala Gln Ser Leu Leu Asp Asn Ser Phe Phe Arg Ala Lys
        280                 285                 290 cgc tac gac ctg gct cgc gtt ggt cgt tac aag atc aac cgc aag ctc    1628
Arg Tyr Asp Leu Ala Arg Val Gly Arg Tyr Lys Ile Asn Arg Lys Leu
    295                 300                 305 ggc ctt ggt ggc gac cac gat ggt ttg atg act ctt act gaa gag gac    1676
Gly Leu Gly Gly Asp His Asp Gly Leu Met Thr Leu Thr Glu Glu Asp
310                 315                 320                 325 atc gca acc acc atc gag tac ctg gtg cgt ctg cac gca ggt gag cgc    1724
Ile Ala Thr Thr Ile Glu Tyr Leu Val Arg Leu His Ala Gly Glu Arg
                330                 335                 340 gtc atg act tct cca aat ggt gaa gag atc cca gtc gag acc gat gac    1772
Val Met Thr Ser Pro Asn Gly Glu Glu Ile Pro Val Glu Thr Asp Asp
            345                 350                 355 atc gac cac ttt ggt aac cgt cgt ctg cgt acc gtt ggc gaa ctg atc    1820
Ile Asp His Phe Gly Asn Arg Arg Leu Arg Thr Val Gly Glu Leu Ile
        360                 365                 370 cag aac cag gtc cgt gtc ggc ctg tcc cgc atg gag cgc gtt gtt cgt    1868
Gln Asn Gln Val Arg Val Gly Leu Ser Arg Met Glu Arg Val Val Arg
    375                 380                 385 gag cgt atg acc acc cag gat gcg gag tcc att act cct act tcc ttg    1916
Glu Arg Met Thr Thr Gln Asp Ala Glu Ser Ile Thr Pro Thr Ser Leu
390                 395                 400                 405 atc aac gtt cgt cct gtc tct gca gct atc cgt gag ttc ttc gga act    1964
Ile Asn Val Arg Pro Val Ser Ala Ala Ile Arg Glu Phe Phe Gly Thr
                410                 415                 420 tcc cag ctg tct cag ttc atg gtc cag aac aac tcc ctg tct ggt ttg    2012
Ser Gln Leu Ser Gln Phe Met Val Gln Asn Asn Ser Leu Ser Gly Leu
            425                 430                 435 act cac aag cgt cgt ctg tcg gct ctg ggc ccg ggt ggt ctg tcc cgt    2060
Thr His Lys Arg Arg Leu Ser Ala Leu Gly Pro Gly Gly Leu Ser Arg
        440                 445                 450 gag cgc gcc ggc atc gag gtt cga gac gtt cac cca tct cac tac ggc    2108
Glu Arg Ala Gly Ile Glu Val Arg Asp Val His Pro Ser His Tyr Gly
    455                 460                 465 cgt atg tgc cca att gag act ccg gaa ggt cca aac att ggc ctg atc    2156
Arg Met Cys Pro Ile Glu Thr Pro Glu Gly Pro Asn Ile Gly Leu Ile
470                 475                 480                 485 ggt tcc ttg gct tcc tat gct cga gtg aac cca ttc ggt ttc att gag    2204
Gly Ser Leu Ala Ser Tyr Ala Arg Val Asn Pro Phe Gly Phe Ile Glu
                490                 495                 500 acc cca tac cgt cgc atc atc gac ggc aag ctg acc gac cag att gac    2252
Thr Pro Tyr Arg Arg Ile Ile Asp Gly Lys Leu Thr Asp Gln Ile Asp
            505                 510                 515 tac ctt acc gct gat gag gaa gac cgc ttc gtt gtt gcg cag gca aac    2300
Tyr Leu Thr Ala Asp Glu Glu Asp Arg Phe Val Val Ala Gln Ala Asn
        520                 525                 530 acg cac tac gac gaa gag ggc aac atc acc gat gag acc gtc act gtt    2348
```

```
                                                             -continued

Thr His Tyr Asp Glu Glu Gly Asn Ile Thr Asp Glu Thr Val Thr Val
    535             540                 545 cgt ctg aag gac ggc gac atc gcc atg gtt ggc cgc aac gcg gtt gat    2396
Arg Leu Lys Asp Gly Asp Ile Ala Met Val Gly Arg Asn Ala Val Asp
550                 555                 560                 565 tac atg gac gtt tcc cct cgt cag atg gtt tct gtt ggt acc gcg atg    2444
Tyr Met Asp Val Ser Pro Arg Gln Met Val Ser Val Gly Thr Ala Met
                570                 575                 580 att cca ttc ctg gag cac gac gat gct aac cgt gca ctg atg ggc gcg    2492
Ile Pro Phe Leu Glu His Asp Asp Ala Asn Arg Ala Leu Met Gly Ala
            585                 590                 595 aac atg cag aag cag gct gtg cca ctg att cgt gcc gag gct cct ttc    2540
Asn Met Gln Lys Gln Ala Val Pro Leu Ile Arg Ala Glu Ala Pro Phe
        600                 605                 610 gtg ggc acc ggt atg gag cag cgc gca gca tac gac gcc ggc gac ctg    2588
Val Gly Thr Gly Met Glu Gln Arg Ala Ala Tyr Asp Ala Gly Asp Leu
    615                 620                 625 gtt att acc cca gtc gca ggt gtg gtg gaa aac gtt tca gct gac ttc    2636
Val Ile Thr Pro Val Ala Gly Val Val Glu Asn Val Ser Ala Asp Phe
630                 635                 640                 645 atc acc atc atg gct gat gac ggc aag cgc gaa acc tac ctg ctg cgt    2684
Ile Thr Ile Met Ala Asp Asp Gly Lys Arg Glu Thr Tyr Leu Leu Arg
                650                 655                 660 aag ttc cag cgc acc aac cag ggc acc agc tac aac cag aag cct ttg    2732
Lys Phe Gln Arg Thr Asn Gln Gly Thr Ser Tyr Asn Gln Lys Pro Leu
            665                 670                 675 gtt aac ttg ggc gag cgc gtt gaa gct ggc cag gtt att gct gat ggt    2780
Val Asn Leu Gly Glu Arg Val Glu Ala Gly Gln Val Ile Ala Asp Gly
        680                 685                 690 cca ggt acc ttc aat ggt gaa atg tcc ctt ggc cgt aac ctt ctg gtt    2828
Pro Gly Thr Phe Asn Gly Glu Met Ser Leu Gly Arg Asn Leu Leu Val
    695                 700                 705 gcg ttc atg cct tgg gaa ggc cac aac tac gag gat gcg atc atc ctc    2876
Ala Phe Met Pro Trp Glu Gly His Asn Tyr Glu Asp Ala Ile Ile Leu
710                 715                 720                 725 aac cag aac atc gtt gag cag gac atc ttg acc tcg atc cac atc gag    2924
Asn Gln Asn Ile Val Glu Gln Asp Ile Leu Thr Ser Ile His Ile Glu
                730                 735                 740 gag cac gag atc gat gcc cgc gac act aag ctt ggc gcc gaa gaa atc    2972
Glu His Glu Ile Asp Ala Arg Asp Thr Lys Leu Gly Ala Glu Glu Ile
            745                 750                 755 acc cgc gac atc cct aat gtg tct gaa gaa gtc ctc aag gac ctc gac    3020
Thr Arg Asp Ile Pro Asn Val Ser Glu Glu Val Leu Lys Asp Leu Asp
        760                 765                 770 gac cgc ggt att gtc cgc atc ggt gct gat gtt cgt gac ggc gac atc    3068
Asp Arg Gly Ile Val Arg Ile Gly Ala Asp Val Arg Asp Gly Asp Ile
    775                 780                 785 ctg gtc ggt aag gtc acc cct aag ggc gag acc gag ctc acc ccg gaa    3116
Leu Val Gly Lys Val Thr Pro Lys Gly Glu Thr Glu Leu Thr Pro Glu
790                 795                 800                 805 gag cgc ttg ctg cgc gca atc ttc ggt gag aag gcc cgc gaa gtt cgc    3164
Glu Arg Leu Leu Arg Ala Ile Phe Gly Glu Lys Ala Arg Glu Val Arg
                810                 815                 820 gat acc tcc atg aag gtg cct cac ggt gag acc ggc aag gtc atc ggc    3212
Asp Thr Ser Met Lys Val Pro His Gly Glu Thr Gly Lys Val Ile Gly
            825                 830                 835 gtg cgt cac ttc tcc cgc gag gac gac gac gat ctg gct cct ggc gtc    3260
Val Arg His Phe Ser Arg Glu Asp Asp Asp Asp Leu Ala Pro Gly Val
        840                 845                 850
```

```
aac gag atg atc cgt atc tac gtt gct cag aag cgt aag atc cag gac      3308
Asn Glu Met Ile Arg Ile Tyr Val Ala Gln Lys Arg Lys Ile Gln Asp
    855                 860                 865 ggc gat aag ctc gct ggc cgc cac ggt aac aag ggt gtt gtc ggt aaa      3356
Gly Asp Lys Leu Ala Gly Arg His Gly Asn Lys Gly Val Val Gly Lys
870                 875                 880                 885 att ttg cct cag gaa gat atg cca ttc ctt cca gac ggc act cct gtt      3404
Ile Leu Pro Gln Glu Asp Met Pro Phe Leu Pro Asp Gly Thr Pro Val
                890                 895                 900 gac atc atc ttg aac acc cac ggt gtt cca cgt cgt atg aac att ggt      3452
Asp Ile Ile Leu Asn Thr His Gly Val Pro Arg Arg Met Asn Ile Gly
            905                 910                 915 cag gtt ctt gag acc cac ctt ggc tgg ctg gca tct gct ggt tgg tcc      3500
Gln Val Leu Glu Thr His Leu Gly Trp Leu Ala Ser Ala Gly Trp Ser
        920                 925                 930 gtg gat cct gaa gat cct gag aac gct gag ctc gtc aag act ctg cct      3548
Val Asp Pro Glu Asp Pro Glu Asn Ala Glu Leu Val Lys Thr Leu Pro
935                 940                 945 gca gac ctc ctc gag gtt cct gct ggt tcc ttg act gca act cct gtg      3596
Ala Asp Leu Leu Glu Val Pro Ala Gly Ser Leu Thr Ala Thr Pro Val
950                 955                 960                 965 ttc gac ggt gcg tca aac gaa gag ctc gca ggc ctg ctc gct aat tca      3644
Phe Asp Gly Ala Ser Asn Glu Glu Leu Ala Gly Leu Leu Ala Asn Ser
                970                 975                 980 cgt cca aac cgc gac ggc gac gtc atg gtt aac gcg gat ggt aaa gca      3692
Arg Pro Asn Arg Asp Gly Asp Val Met Val Asn Ala Asp Gly Lys Ala
            985                 990                 995 acg ctt atc gac ggt cgc tcc ggt gag cct tac ccg tac ccg gtt          3737
Thr Leu Ile Asp Gly Arg Ser Gly Glu Pro Tyr Pro Tyr Pro Val
        1000                1005                1010 tcc atc ggc tac atg tac atg ctg aag ctg cac cac ctc gtt gac          3782
Ser Ile Gly Tyr Met Tyr Met Leu Lys Leu His His Leu Val Asp
1015                1020                1025 gag aag atc cac gca cgt tcc act ggt cct tac tcc atg att acc          3827
Glu Lys Ile His Ala Arg Ser Thr Gly Pro Tyr Ser Met Ile Thr
            1030                1035                1040 cag cag cca ctg ggt ggt aaa gca cag ttc ggt gga cag cgt ttc          3872
Gln Gln Pro Leu Gly Gly Lys Ala Gln Phe Gly Gly Gln Arg Phe
        1045                1050                1055 ggc gaa atg gag gtg tgg gca atg cag gca tac ggc gct gcc tac          3917
Gly Glu Met Glu Val Trp Ala Met Gln Ala Tyr Gly Ala Ala Tyr
1060                1065                1070 aca ctt cag gag ctg ctg acc atc aag tct gat gac gtg gtt ggc          3962
Thr Leu Gln Glu Leu Leu Thr Ile Lys Ser Asp Asp Val Val Gly
    1075                1080                1085 cgt gtc aag gtc tac gaa gca att gtg aag ggc gag aac atc ccg          4007
Arg Val Lys Val Tyr Glu Ala Ile Val Lys Gly Glu Asn Ile Pro
                1090                1095                1100 gat cca ggt att cct gag tcc ttc aag gtt ctc ctc aag gag ctc          4052
Asp Pro Gly Ile Pro Glu Ser Phe Lys Val Leu Leu Lys Glu Leu
            1105                1110                1115 cag tcc ttg tgc ctg aac gtg gag gtt ctc tcc gca gac ggc act          4097
Gln Ser Leu Cys Leu Asn Val Glu Val Leu Ser Ala Asp Gly Thr
        1120                1125                1130 cca atg gag ctc gcg ggt gac gac gac gac ttc gat cag gca ggc          4142
Pro Met Glu Leu Ala Gly Asp Asp Asp Asp Phe Asp Gln Ala Gly
1135                1140                1145 gcc tca ctt ggc atc aac ctg tcc cgt gac gag cgt tcc gac gcc          4187
Ala Ser Leu Gly Ile Asn Leu Ser Arg Asp Glu Arg Ser Asp Ala
    1150                1155                1160
```

-continued

```
gac acc gca  tagcagatca gaaaacaacc gctagaaatc aagccataca         4236
Asp Thr Ala
        1165 tcccccggac attgaagaga tgttctgggg ggaaagggag ttttacgtgc tcgacgtaaa  4296 cgtcttcgat gagctccgca tcggcctggc caccgccgac gacatccgcc gttggtccaa  4356 gggtgaggtc aagaagccgg agaccatcaa ctaccgaacc ctcaagcctg agaaggacgg  4416 tctgttctgc gagcgtatct tcggtccaac tcgcgactgg gagtgcgcct gcggtaagta  4476 caagcgtgtc cgctacaagg gcatcatctg tgaacgctgt ggcgttgagg tcaccaagtc  4536 caaggtgcgc cgtgagcgca tgggacacat tgagctcgct gcaccagtaa cccacatttg  4596 gtacttcaag ggcgttccat cacgcctcgg ctacctttg gaccttgctc caaaggacct   4656 ggacctcatc atctacttcg gtgcgaacat catcaccagc gtggacgaag aggctcgcca  4716 cagcgaccag accactcttg aggcagaaat gcttctggag aagaaggacg ttgaggcaga  4776 cgcagagtct gacattgctg agcgtgctga aaagctcgaa gaggatcttg ctgaacttga  4836 ggcagctggc gctaaggccg acgctcgccg caaggttcag gctgctgccg ataaggaaat  4896 gcagcacatc cgtgagcgtg cacagcgcga aatcgatcgt ctcgatgagg tctggcagac  4956 cttcatcaag cttgctccaa agcagatgat ccgcgatgag aagctctacg atgaactgat  5016 cgaccgctac gaggattact tcaccggtgg tatgggtgca gagtccattg aggctttgat  5076 ccagaacttc gaccttgatg ctg                                          5099
```

```
<210> SEQ ID NO 4
<211> LENGTH: 1165
<212> TYPE: PRT
<213> ORGANISM: Corynebacterium glutamicum

<400> SEQUENCE: 4
```

```
Val Leu Glu Gly Leu Ile Leu Ala Val Ser Arg Gln Thr Lys Ser Val
1               5                   10                  15

Val Asp Ile Pro Gly Ala Pro Gln Arg Tyr Ser Phe Ala Lys Val Ser
            20                  25                  30

Ala Pro Ile Glu Val Pro Gly Leu Leu Asp Leu Gln Leu Asp Ser Tyr
        35                  40                  45

Ser Trp Leu Ile Gly Thr Pro Glu Trp Arg Ala Arg Gln Lys Glu Glu
    50                  55                  60

Phe Gly Glu Gly Ala Arg Val Thr Ser Gly Leu Glu Asn Ile Leu Glu
65                  70                  75                  80

Glu Leu Ser Pro Ile Gln Asp Tyr Ser Gly Asn Met Ser Leu Ser Leu
                85                  90                  95

Ser Glu Pro Arg Phe Glu Asp Val Lys Asn Thr Ile Asp Glu Ala Lys
            100                 105                 110

Glu Lys Asp Ile Asn Tyr Ala Ala Pro Leu Tyr Val Thr Ala Glu Phe
        115                 120                 125

Val Asn Asn Thr Thr Gly Glu Ile Lys Ser Gln Thr Val Phe Ile Gly
    130                 135                 140

Asp Phe Pro Met Met Thr Asp Lys Gly Thr Phe Ile Ile Asn Gly Thr
145                 150                 155                 160

Glu Arg Val Val Val Ser Gln Leu Val Arg Ser Pro Gly Val Tyr Phe
                165                 170                 175

Asp Gln Thr Ile Asp Lys Ser Thr Glu Arg Pro Leu His Ala Val Lys
            180                 185                 190
```

-continued

```
Val Ile Pro Phe Arg Gly Ala Trp Leu Glu Phe Asp Val Asp Lys Arg
        195                 200                 205

Asp Ser Val Gly Val Arg Ile Asp Arg Lys Arg Gln Pro Val Thr
    210                 215                 220

Val Leu Leu Lys Ala Leu Gly Trp Thr Thr Glu Gln Ile Thr Glu Arg
225                 230                 235                 240

Phe Gly Phe Ser Glu Ile Met Met Ser Thr Leu Glu Ser Asp Gly Val
                245                 250                 255

Ala Asn Thr Asp Glu Ala Leu Leu Glu Ile Tyr Arg Lys Gln Arg Pro
            260                 265                 270

Gly Glu Gln Pro Thr Arg Asp Leu Ala Gln Ser Leu Leu Asp Asn Ser
        275                 280                 285

Phe Phe Arg Ala Lys Arg Tyr Asp Leu Ala Arg Val Gly Arg Tyr Lys
    290                 295                 300

Ile Asn Arg Lys Leu Gly Leu Gly Gly Asp His Asp Gly Leu Met Thr
305                 310                 315                 320

Leu Thr Glu Glu Asp Ile Ala Thr Thr Ile Glu Tyr Leu Val Arg Leu
                325                 330                 335

His Ala Gly Glu Arg Val Met Thr Ser Pro Asn Gly Glu Glu Ile Pro
            340                 345                 350

Val Glu Thr Asp Asp Ile Asp His Phe Gly Asn Arg Arg Leu Arg Thr
        355                 360                 365

Val Gly Glu Leu Ile Gln Asn Gln Val Arg Val Gly Leu Ser Arg Met
    370                 375                 380

Glu Arg Val Val Arg Glu Arg Met Thr Thr Gln Asp Ala Glu Ser Ile
385                 390                 395                 400

Thr Pro Thr Ser Leu Ile Asn Val Arg Pro Val Ser Ala Ala Ile Arg
                405                 410                 415

Glu Phe Phe Gly Thr Ser Gln Leu Ser Gln Phe Met Val Gln Asn Asn
            420                 425                 430

Ser Leu Ser Gly Leu Thr His Lys Arg Arg Leu Ser Ala Leu Gly Pro
        435                 440                 445

Gly Gly Leu Ser Arg Glu Arg Ala Gly Ile Glu Val Arg Asp Val His
    450                 455                 460

Pro Ser His Tyr Gly Arg Met Cys Pro Ile Glu Thr Pro Glu Gly Pro
465                 470                 475                 480

Asn Ile Gly Leu Ile Gly Ser Leu Ala Ser Tyr Ala Arg Val Asn Pro
                485                 490                 495

Phe Gly Phe Ile Glu Thr Pro Tyr Arg Arg Ile Ile Asp Gly Lys Leu
            500                 505                 510

Thr Asp Gln Ile Asp Tyr Leu Thr Ala Asp Glu Glu Asp Arg Phe Val
        515                 520                 525

Val Ala Gln Ala Asn Thr His Tyr Asp Glu Glu Gly Asn Ile Thr Asp
    530                 535                 540

Glu Thr Val Thr Val Arg Leu Lys Asp Gly Asp Ile Ala Met Val Gly
545                 550                 555                 560

Arg Asn Ala Val Asp Tyr Met Asp Val Ser Pro Arg Gln Met Val Ser
                565                 570                 575

Val Gly Thr Ala Met Ile Pro Phe Leu Glu His Asp Asp Ala Asn Arg
            580                 585                 590

Ala Leu Met Gly Ala Asn Met Gln Lys Gln Ala Val Pro Leu Ile Arg
        595                 600                 605

Ala Glu Ala Pro Phe Val Gly Thr Gly Met Glu Gln Arg Ala Ala Tyr
```

-continued

```
            610                 615                 620
Asp Ala Gly Asp Leu Val Ile Thr Pro Val Ala Gly Val Val Glu Asn
625                 630                 635                 640

Val Ser Ala Asp Phe Ile Thr Ile Met Ala Asp Gly Lys Arg Glu
                645                 650                 655

Thr Tyr Leu Leu Arg Lys Phe Gln Arg Thr Asn Gln Gly Thr Ser Tyr
            660                 665                 670

Asn Gln Lys Pro Leu Val Asn Leu Gly Glu Arg Val Glu Ala Gly Gln
                675                 680                 685

Val Ile Ala Asp Gly Pro Gly Thr Phe Asn Gly Glu Met Ser Leu Gly
690                 695                 700

Arg Asn Leu Leu Val Ala Phe Met Pro Trp Glu Gly His Asn Tyr Glu
705                 710                 715                 720

Asp Ala Ile Ile Leu Asn Gln Asn Ile Val Glu Gln Asp Ile Leu Thr
                725                 730                 735

Ser Ile His Ile Glu Glu His Glu Ile Asp Ala Arg Asp Thr Lys Leu
                740                 745                 750

Gly Ala Glu Glu Ile Thr Arg Asp Ile Pro Asn Val Ser Glu Glu Val
                755                 760                 765

Leu Lys Asp Leu Asp Asp Arg Gly Ile Val Arg Ile Gly Ala Asp Val
770                 775                 780

Arg Asp Gly Asp Ile Leu Val Gly Lys Val Thr Pro Lys Gly Glu Thr
785                 790                 795                 800

Glu Leu Thr Pro Glu Glu Arg Leu Leu Arg Ala Ile Phe Gly Glu Lys
                805                 810                 815

Ala Arg Glu Val Arg Asp Thr Ser Met Lys Val Pro His Gly Glu Thr
                820                 825                 830

Gly Lys Val Ile Gly Val Arg His Phe Ser Arg Glu Asp Asp Asp
                835                 840                 845

Leu Ala Pro Gly Val Asn Glu Met Ile Arg Ile Tyr Val Ala Gln Lys
                850                 855                 860

Arg Lys Ile Gln Asp Gly Asp Lys Leu Ala Gly Arg His Gly Asn Lys
865                 870                 875                 880

Gly Val Val Gly Lys Ile Leu Pro Gln Glu Asp Met Pro Phe Leu Pro
                885                 890                 895

Asp Gly Thr Pro Val Asp Ile Ile Leu Asn Thr His Gly Val Pro Arg
                900                 905                 910

Arg Met Asn Ile Gly Gln Val Leu Glu Thr His Leu Gly Trp Leu Ala
                915                 920                 925

Ser Ala Gly Trp Ser Val Asp Pro Glu Asp Pro Glu Asn Ala Glu Leu
                930                 935                 940

Val Lys Thr Leu Pro Ala Asp Leu Leu Glu Val Pro Ala Gly Ser Leu
945                 950                 955                 960

Thr Ala Thr Pro Val Phe Asp Gly Ala Ser Asn Glu Glu Leu Ala Gly
                965                 970                 975

Leu Leu Ala Asn Ser Arg Pro Asn Arg Asp Gly Asp Val Met Val Asn
                980                 985                 990

Ala Asp Gly Lys Ala Thr Leu Ile Asp Gly Arg Ser Gly Glu Pro Tyr
                995                 1000                1005

Pro Tyr Pro Val Ser Ile Gly Tyr Met Tyr Met Leu Lys Leu His
    1010                1015                1020

His Leu Val Asp Glu Lys Ile His Ala Arg Ser Thr Gly Pro Tyr
    1025                1030                1035
```

```
Ser Met Ile Thr Gln Gln Pro Leu Gly Gly Lys Ala Gln Phe Gly
    1040                1045                1050

Gly Gln Arg Phe Gly Glu Met Glu Val Trp Ala Met Gln Ala Tyr
        1055                1060                1065

Gly Ala Ala Tyr Thr Leu Gln Glu Leu Leu Thr Ile Lys Ser Asp
        1070                1075                1080

Asp Val Val Gly Arg Val Lys Val Tyr Glu Ala Ile Val Lys Gly
        1085                1090                1095

Glu Asn Ile Pro Asp Pro Gly Ile Pro Glu Ser Phe Lys Val Leu
        1100                1105                1110

Leu Lys Glu Leu Gln Ser Leu Cys Leu Asn Val Glu Val Leu Ser
        1115                1120                1125

Ala Asp Gly Thr Pro Met Glu Leu Ala Gly Asp Asp Asp Asp Phe
        1130                1135                1140

Asp Gln Ala Gly Ala Ser Leu Gly Ile Asn Leu Ser Arg Asp Glu
        1145                1150                1155

Arg Ser Asp Ala Asp Thr Ala
        1160                1165

<210> SEQ ID NO 5
<211> LENGTH: 5099
<212> TYPE: DNA
<213> ORGANISM: Corynebacterium glutamicum
<220> FEATURE:
<221> NAME/KEY: CDS
<222> LOCATION: (702)..(4196)

<400> SEQUENCE: 5
acaatgtgac tcgtgatttt tgggtggatc agcgtaccgg tttggttgtc gatctagctg      60
aaaatattga tgatttttac ggcgaccgca gcggccagaa gtacgaacag aaattgcttt     120
tcgacgcctc cctcgacgat gcagctgtct ctaagctggt tgcacaggcc gaaagcatcc     180
ctgatggaga tgtgagcaaa atcgcaaata ccgtaggtat tgtgatcggt gcggtattgg     240
ctctcgtggg cctggccggg tgttttgggg cgtttgggaa gaaacgtcga gaagcttaac     300
ctgctgttca atagattttt ccctgtttcg aattgcggaa accccgggtt tgtttgctag     360
ggtgcctcgt agaaggggtc aagaagattt ctgggaaacg cgcccgtgcg gttggttgct     420
aatagcacgc ggagcaccag atgaaaaatc tcccctttac tttcgcgcgc gattggtata     480
ctctgagtcg ttgcgttgga attcgtgact ctttttcgtt cctgtagcgc caagaccttg     540
atcaaggtgg tttaaaaaaa ccgatttgac aaggtcattc agtgctatct ggagtcgttc     600
agggggatcg ggttcctcag cagaccaatt gctcaaaaat accagcggtg ttgatctgca     660
cttaatggcc ttgaccagcc aggtgcaatt acccgcgtga g gtg ctg gaa gga ccc    716
                                              Val Leu Glu Gly Pro
                                                1               5 atc ttg gca gtc tcc cgc cag acc aag tca gtc gtc gat att ccc ggt       764
Ile Leu Ala Val Ser Arg Gln Thr Lys Ser Val Val Asp Ile Pro Gly
              10                  15                  20 gca ccg cag cgt tat tct ttc gcg aag gtg tcc gca ccc att gag gtg       812
Ala Pro Gln Arg Tyr Ser Phe Ala Lys Val Ser Ala Pro Ile Glu Val
          25                  30                  35 ccc ggg cta cta gat ctt caa ctg gat tct tac tcc tgg ctg att ggt       860
Pro Gly Leu Leu Asp Leu Gln Leu Asp Ser Tyr Ser Trp Leu Ile Gly
      40                  45                  50 acg cct gag tgg cgt gct cgt cag aag gaa gaa ttc ggc gag gga gcc       908
Thr Pro Glu Trp Arg Ala Arg Gln Lys Glu Glu Phe Gly Glu Gly Ala
```

```
                   55                  60                  65
cgc gta acc agc ggc ctt gag aac att ctc gag gag ctc tcc cca atc    956
Arg Val Thr Ser Gly Leu Glu Asn Ile Leu Glu Glu Leu Ser Pro Ile
 70              75                  80                  85 cag gat tac tct gga aac atg tcc ctg agc ctt tcg gag cca cgc ttc   1004
Gln Asp Tyr Ser Gly Asn Met Ser Leu Ser Leu Ser Glu Pro Arg Phe
                 90                  95                 100 gaa gac gtc aag aac acc att gac gag gcg aaa gaa aag gac atc aac   1052
Glu Asp Val Lys Asn Thr Ile Asp Glu Ala Lys Glu Lys Asp Ile Asn
                105                 110                 115 tac gcg gcg cca ctg tat gtg acc gcg gag ttc gtc aac aac acc acc   1100
Tyr Ala Ala Pro Leu Tyr Val Thr Ala Glu Phe Val Asn Asn Thr Thr
            120                 125                 130 ggt gaa atc aag tct cag act gtc ttc atc ggc gat ttc cca atg atg   1148
Gly Glu Ile Lys Ser Gln Thr Val Phe Ile Gly Asp Phe Pro Met Met
        135                 140                 145 acg gac aag gga acg ttc atc atc aac gga acc gaa cgc gtt gtg gtc   1196
Thr Asp Lys Gly Thr Phe Ile Ile Asn Gly Thr Glu Arg Val Val Val
150                 155                 160                 165 agc cag ctc gtc cgc tcc ccg ggc gtg tac ttt gac cag acc atc gat   1244
Ser Gln Leu Val Arg Ser Pro Gly Val Tyr Phe Asp Gln Thr Ile Asp
                170                 175                 180 aag tca act gag cgt cca ctg cac gcc gtg aag gtt att cct tcc cgt   1292
Lys Ser Thr Glu Arg Pro Leu His Ala Val Lys Val Ile Pro Ser Arg
            185                 190                 195 ggt gct tgg ctt gag ttt gac gtc gat aag cgc gat tcg gtt ggt gtt   1340
Gly Ala Trp Leu Glu Phe Asp Val Asp Lys Arg Asp Ser Val Gly Val
        200                 205                 210 cgt att gac cgc aag cgt cgc cag cca gtc acc gta ctg ctg aag gct   1388
Arg Ile Asp Arg Lys Arg Arg Gln Pro Val Thr Val Leu Leu Lys Ala
215                 220                 225 ctt ggc tgg acc act gag cag atc acc gag cgt ttc ggt ttc tct gaa   1436
Leu Gly Trp Thr Thr Glu Gln Ile Thr Glu Arg Phe Gly Phe Ser Glu
230                 235                 240                 245 atc atg atg tcc acc ctc gag tcc gat ggt gta gca aac acc gat gag   1484
Ile Met Met Ser Thr Leu Glu Ser Asp Gly Val Ala Asn Thr Asp Glu
                250                 255                 260 gca ttg ctg gag atc tac cgc aag cag cgt cca ggc gag cag cct acc   1532
Ala Leu Leu Glu Ile Tyr Arg Lys Gln Arg Pro Gly Glu Gln Pro Thr
            265                 270                 275 cgc gac ctt gcg cag tcc ctc ctg gac aac agc ttc ttc cgt gca aag   1580
Arg Asp Leu Ala Gln Ser Leu Leu Asp Asn Ser Phe Phe Arg Ala Lys
        280                 285                 290 cgc tac gac ctg gct cgc gtt ggt cgt tac aag atc aac cgc aag ctc   1628
Arg Tyr Asp Leu Ala Arg Val Gly Arg Tyr Lys Ile Asn Arg Lys Leu
295                 300                 305 ggc ctt ggt ggc gac cac gat ggt ttg atg act ttg act gaa gag gac   1676
Gly Leu Gly Gly Asp His Asp Gly Leu Met Thr Leu Thr Glu Glu Asp
310                 315                 320                 325 atc gca acc acc atc gag tac ctg gtg cgt ctg cac gca ggt gag cgc   1724
Ile Ala Thr Thr Ile Glu Tyr Leu Val Arg Leu His Ala Gly Glu Arg
                330                 335                 340 gtc atg act tct cca aat ggt gaa gag atc cca gtc gag acc gat gac   1772
Val Met Thr Ser Pro Asn Gly Glu Glu Ile Pro Val Glu Thr Asp Asp
            345                 350                 355 atc gac cac ttt ggt aac cgt cgt ctg cgt acc gtt ggc gaa ctg atc   1820
Ile Asp His Phe Gly Asn Arg Arg Leu Arg Thr Val Gly Glu Leu Ile
        360                 365                 370 cag aac cag gtc cgt gtc ggc ctg tcc cgc atg gag cgc gtt gtt cgt   1868
```

-continued

```
        Gln Asn Gln Val Arg Val Gly Leu Ser Arg Met Glu Arg Val Val Arg
            375                 380                 385 gag cgt atg acc acc cag gat gcg gag tcc att act cct act tcc ttg           1916
Glu Arg Met Thr Thr Gln Asp Ala Glu Ser Ile Thr Pro Thr Ser Leu
390                 395                 400                 405 atc aac gtt cgt cct gtc tct gca gct atc cgt gag ttc ttc gga act           1964
Ile Asn Val Arg Pro Val Ser Ala Ala Ile Arg Glu Phe Phe Gly Thr
                410                 415                 420 tcc cag ctg tct cag ttc atg gac cag aac aac tcc ctg tct ggt ttg           2012
Ser Gln Leu Ser Gln Phe Met Asp Gln Asn Asn Ser Leu Ser Gly Leu
            425                 430                 435 act tac aag cgt cgt ctg tcg gct ctg ggc ccg ggt ggt ctg tcc cgt           2060
Thr Tyr Lys Arg Arg Leu Ser Ala Leu Gly Pro Gly Gly Leu Ser Arg
        440                 445                 450 gag cgc gcc ggc atc gag gtt cga gac gtt cac cca tct cac tac ggc           2108
Glu Arg Ala Gly Ile Glu Val Arg Asp Val His Pro Ser His Tyr Gly
    455                 460                 465 cgt atg tgc cca att gag act ccg gaa ggt cca aac att ggc ctg atc           2156
Arg Met Cys Pro Ile Glu Thr Pro Glu Gly Pro Asn Ile Gly Leu Ile
470                 475                 480                 485 ggt tcc ttg gct tcc tat gct cga gtg aac cca ttc ggt ttc att gag           2204
Gly Ser Leu Ala Ser Tyr Ala Arg Val Asn Pro Phe Gly Phe Ile Glu
                490                 495                 500 acc cca tac cgt cgc atc atc gac ggc aag ctg acc gac cag att gac           2252
Thr Pro Tyr Arg Arg Ile Ile Asp Gly Lys Leu Thr Asp Gln Ile Asp
            505                 510                 515 tac ctt acc gct gat gag gaa gac cgc ttc gtt gtt gcg cag gca aac           2300
Tyr Leu Thr Ala Asp Glu Glu Asp Arg Phe Val Val Ala Gln Ala Asn
        520                 525                 530 acg cac tac gac gaa gag ggc aac atc acc gat gag acc gtc act gtt           2348
Thr His Tyr Asp Glu Glu Gly Asn Ile Thr Asp Glu Thr Val Thr Val
    535                 540                 545 cgt ctg aag gac ggc gac atc gcc atg gtt ggc cgc aac gcg gtt gat           2396
Arg Leu Lys Asp Gly Asp Ile Ala Met Val Gly Arg Asn Ala Val Asp
550                 555                 560                 565 tac atg gac gtt tcc cct cgt cag atg gtt tct gtt ggt acc gcg atg           2444
Tyr Met Asp Val Ser Pro Arg Gln Met Val Ser Val Gly Thr Ala Met
                570                 575                 580 att cca ttc ctg gag cac gac gat gct aac cgt gca ctg atg ggc gcg           2492
Ile Pro Phe Leu Glu His Asp Asp Ala Asn Arg Ala Leu Met Gly Ala
            585                 590                 595 aac atg cag aag cag gct gtg cca ctg att cgt gcc gag gct cct ttc           2540
Asn Met Gln Lys Gln Ala Val Pro Leu Ile Arg Ala Glu Ala Pro Phe
        600                 605                 610 gtg ggc acc ggt atg gag cag cgc gca gca tac gac gcc ggc gac ctg           2588
Val Gly Thr Gly Met Glu Gln Arg Ala Ala Tyr Asp Ala Gly Asp Leu
    615                 620                 625 gtt att acc cca gtc gca ggt gtg gtg gaa aac gtt tca gct gac ttc           2636
Val Ile Thr Pro Val Ala Gly Val Val Glu Asn Val Ser Ala Asp Phe
630                 635                 640                 645 atc acc atc atg gct gat gac ggc aag cgc gaa acc tac ctg ctg cgt           2684
Ile Thr Ile Met Ala Asp Asp Gly Lys Arg Glu Thr Tyr Leu Leu Arg
                650                 655                 660 aag ttc cag cgc acc aac cag ggc acc agc tac aac cag aag cct ttg           2732
Lys Phe Gln Arg Thr Asn Gln Gly Thr Ser Tyr Asn Gln Lys Pro Leu
            665                 670                 675 gtt aac ttg ggc gag cgc gtt gaa gct ggc cag gtt att gct gat ggt           2780
Val Asn Leu Gly Glu Arg Val Glu Ala Gly Gln Val Ile Ala Asp Gly
        680                 685                 690
```

```
cca ggt acc ttc aat ggt gaa atg tcc ctt ggc cgt aac ctt ctg gtt      2828
Pro Gly Thr Phe Asn Gly Glu Met Ser Leu Gly Arg Asn Leu Leu Val
695                 700                 705 gcg ttc atg cct tgg gaa ggc cac aac tac gag gat gcg atc atc ctc      2876
Ala Phe Met Pro Trp Glu Gly His Asn Tyr Glu Asp Ala Ile Ile Leu
710                 715                 720                 725 aac cag aac atc gtt gag cag gac atc ttg acc tcg atc cac atc gag      2924
Asn Gln Asn Ile Val Glu Gln Asp Ile Leu Thr Ser Ile His Ile Glu
            730                 735                 740 gag cac gag atc gat gcc cgc gac act aag ctt ggc gcc gaa gaa atc      2972
Glu His Glu Ile Asp Ala Arg Asp Thr Lys Leu Gly Ala Glu Glu Ile
        745                 750                 755 acc cgc gac atc cct aat gtg tct gaa gaa gtc ctc aag gac ctc gac      3020
Thr Arg Asp Ile Pro Asn Val Ser Glu Glu Val Leu Lys Asp Leu Asp
    760                 765                 770 gac cgc ggt att gtc cgc atc ggt gct gat gtt cgt gac ggc gac atc      3068
Asp Arg Gly Ile Val Arg Ile Gly Ala Asp Val Arg Asp Gly Asp Ile
775                 780                 785 ctg gtc ggt aag gtc acc cct aag ggc gag acc gag ctc acc ccg gaa      3116
Leu Val Gly Lys Val Thr Pro Lys Gly Glu Thr Glu Leu Thr Pro Glu
790                 795                 800                 805 gag cgc ttg ctg cgc gca atc ttc ggt gag aag gcc cgc gaa gtt cgc      3164
Glu Arg Leu Leu Arg Ala Ile Phe Gly Glu Lys Ala Arg Glu Val Arg
            810                 815                 820 gat acc tcc atg aag gtg cct cac ggt gag acc ggc aag gtc atc ggc      3212
Asp Thr Ser Met Lys Val Pro His Gly Glu Thr Gly Lys Val Ile Gly
        825                 830                 835 gtg cgt cac ttc tcc cgc gag gac gac gac gat ctg gct cct ggc gtc      3260
Val Arg His Phe Ser Arg Glu Asp Asp Asp Asp Leu Ala Pro Gly Val
    840                 845                 850 aac gag atg atc cgt atc tac gtt gct cag aag cgt aag atc cag gac      3308
Asn Glu Met Ile Arg Ile Tyr Val Ala Gln Lys Arg Lys Ile Gln Asp
855                 860                 865 ggc gat aag ctc gct ggc cgc cac ggt aac aag ggt gtt gtc ggt aaa      3356
Gly Asp Lys Leu Ala Gly Arg His Gly Asn Lys Gly Val Val Gly Lys
870                 875                 880                 885 att ttg cct cag gaa gat atg cca ttc ctt cca gac ggc act cct gtt      3404
Ile Leu Pro Gln Glu Asp Met Pro Phe Leu Pro Asp Gly Thr Pro Val
            890                 895                 900 gac atc atc ttg aac acc cac ggt gtt cca cgt cgt atg aac att ggt      3452
Asp Ile Ile Leu Asn Thr His Gly Val Pro Arg Arg Met Asn Ile Gly
        905                 910                 915 cag gtt ctt gag acc cac ctt ggc tgg ctg gca tct gct ggt tgg tcc      3500
Gln Val Leu Glu Thr His Leu Gly Trp Leu Ala Ser Ala Gly Trp Ser
    920                 925                 930 gtg gat cct gaa gat cct gag aac gct gag ctc gtc aag act ctg cct      3548
Val Asp Pro Glu Asp Pro Glu Asn Ala Glu Leu Val Lys Thr Leu Pro
935                 940                 945 gca gac ctc ctc gag gtt cct gct ggt tcc ttg act gca act cct gtg      3596
Ala Asp Leu Leu Glu Val Pro Ala Gly Ser Leu Thr Ala Thr Pro Val
950                 955                 960                 965 ttc gac ggt gcg tca aac gaa gag ctc gca ggc ctg ctc gct aat tca      3644
Phe Asp Gly Ala Ser Asn Glu Glu Leu Ala Gly Leu Leu Ala Asn Ser
            970                 975                 980 cgt cca aac cgc gac ggc gac gtc atg gtt aac gcg gat ggt aaa gca      3692
Arg Pro Asn Arg Asp Gly Asp Val Met Val Asn Ala Asp Gly Lys Ala
        985                 990                 995 acg ctt atc gac ggt cgc tcc ggt gag cct tac ccg tac ccg gtt          3737
Thr Leu Ile Asp Gly Arg Ser Gly Glu Pro Tyr Pro Tyr Pro Val
    1000                1005                1010
```

| | | |
|---|---|---|
| tcc atc ggc tac atg tac atg ctg aag ctg cac cac ctc gtt gac<br>Ser Ile Gly Tyr Met Tyr Met Leu Lys Leu His His Leu Val Asp<br>1015 1020 1025 | | 3782 |
| gag aag atc cac gca cgt tcc act ggt cct tac tcc atg att acc<br>Glu Lys Ile His Ala Arg Ser Thr Gly Pro Tyr Ser Met Ile Thr<br>1030 1035 1040 | | 3827 |
| cag cag cca ctg ggt ggt aaa gca cag ttc ggt gga cag cgt ttc<br>Gln Gln Pro Leu Gly Gly Lys Ala Gln Phe Gly Gly Gln Arg Phe<br>1045 1050 1055 | | 3872 |
| ggc gaa atg gag gtg tgg gca atg cag gca tac ggc gct gcc tac<br>Gly Glu Met Glu Val Trp Ala Met Gln Ala Tyr Gly Ala Ala Tyr<br>1060 1065 1070 | | 3917 |
| aca ctt cag gag ctg ctg acc atc aag tct gat gac gtg gtt ggc<br>Thr Leu Gln Glu Leu Leu Thr Ile Lys Ser Asp Asp Val Val Gly<br>1075 1080 1085 | | 3962 |
| cgt gtc aag gtc tac gaa gca att gtg aag ggc gag aac atc ccg<br>Arg Val Lys Val Tyr Glu Ala Ile Val Lys Gly Glu Asn Ile Pro<br>1090 1095 1100 | | 4007 |
| gat cca ggt att cct gag tcc ttc aag gtt ctc ctc aag gag ctc<br>Asp Pro Gly Ile Pro Glu Ser Phe Lys Val Leu Leu Lys Glu Leu<br>1105 1110 1115 | | 4052 |
| cag tcc ttg tgc ctg aac gtg gag gtt ctc tcc gca gac ggc act<br>Gln Ser Leu Cys Leu Asn Val Glu Val Leu Ser Ala Asp Gly Thr<br>1120 1125 1130 | | 4097 |
| cca atg gag ctc gcg ggt gac gac gac gac ttc gat cag gca ggc<br>Pro Met Glu Leu Ala Gly Asp Asp Asp Asp Phe Asp Gln Ala Gly<br>1135 1140 1145 | | 4142 |
| gcc tca ctt ggc atc aac ctg tcc cgt gac gag cgt tcc gac gcc<br>Ala Ser Leu Gly Ile Asn Leu Ser Arg Asp Glu Arg Ser Asp Ala<br>1150 1155 1160 | | 4187 |
| gac acc gca tagcagatca gaaaacaacc gctagaaatc aagccataca<br>Asp Thr Ala<br>1165 | | 4236 |
| tcccccggac attgaagaga tgttctgggg ggaaagggag ttttacgtgc tcgacgtaaa | | 4296 |
| cgtcttcgat gagctccgca tcggcctggc caccgccgac gacatccgcc gttggtccaa | | 4356 |
| gggtgaggtc aagaagccgg agaccatcaa ctaccgaacc ctcaagcctg agaaggacgg | | 4416 |
| tctgttctgc gagcgtatct tcggtccaac tcgcgactgg gagtgcgcct gcggtaagta | | 4476 |
| caagcgtgtc cgctacaagg gcatcatctg tgaacgctgt ggcgttgagg tcaccaagtc | | 4536 |
| caaggtgcgc cgtgagcgca tgggacacat tgagctcgct gcaccagtaa cccacatttg | | 4596 |
| gtacttcaag ggcgttccat cacgcctcgg ctacctttg gaccttgctc caaaggaccct | | 4656 |
| ggacctcatc atctacttcg gtgcgaacat catcaccagc gtggacgaag aggctcgcca | | 4716 |
| cagcgaccag accactcttg aggcagaaat gcttctggag aagaaggacg ttgaggcaga | | 4776 |
| cgcagagtct gacattgctg agcgtgctga aaagctcgaa gaggatcttg ctgaacttga | | 4836 |
| ggcagctggc gctaaggccg acgctcgccg caaggttcag gctgctgccg ataaggaaat | | 4896 |
| gcagcacatc cgtgagcgtg cacagcgcga atcgatcgt ctcgatgagg tctggcagac | | 4956 |
| cttcatcaag cttgctccaa agcagatgat ccgcgatgag aagctctacg atgaactgat | | 5016 |
| cgaccgctac gaggattact tcaccggtgg tatgggtgca gagtccattg aggctttgat | | 5076 |
| ccagaacttc gaccttgatg ctg | | 5099 |

<210> SEQ ID NO 6
<211> LENGTH: 1165
<212> TYPE: PRT

<213> ORGANISM: Corynebacterium glutamicum

<400> SEQUENCE: 6

| | | | | | | | | | | | | | | |
|---|---|---|---|---|---|---|---|---|---|---|---|---|---|---|
| Val | Leu | Glu | Gly | Pro | Ile | Leu | Ala | Val | Ser | Arg | Gln | Thr | Lys | Ser | Val |
| 1 | | | | 5 | | | | | 10 | | | | | 15 | |
| Val | Asp | Ile | Pro | Gly | Ala | Pro | Gln | Arg | Tyr | Ser | Phe | Ala | Lys | Val | Ser |
| | | | 20 | | | | | 25 | | | | | 30 | | |
| Ala | Pro | Ile | Glu | Val | Pro | Gly | Leu | Leu | Asp | Leu | Gln | Leu | Asp | Ser | Tyr |
| | | | 35 | | | | 40 | | | | | 45 | | | |
| Ser | Trp | Leu | Ile | Gly | Thr | Pro | Glu | Trp | Arg | Ala | Arg | Gln | Lys | Glu | Glu |
| | | 50 | | | | | 55 | | | | 60 | | | | |
| Phe | Gly | Glu | Gly | Ala | Arg | Val | Thr | Ser | Gly | Leu | Glu | Asn | Ile | Leu | Glu |
| 65 | | | | | 70 | | | | | 75 | | | | | 80 |
| Glu | Leu | Ser | Pro | Ile | Gln | Asp | Tyr | Ser | Gly | Asn | Met | Ser | Leu | Ser | Leu |
| | | | | 85 | | | | | 90 | | | | | 95 | |
| Ser | Glu | Pro | Arg | Phe | Glu | Asp | Val | Lys | Asn | Thr | Ile | Asp | Glu | Ala | Lys |
| | | | 100 | | | | | 105 | | | | | 110 | | |
| Glu | Lys | Asp | Ile | Asn | Tyr | Ala | Ala | Pro | Leu | Tyr | Val | Thr | Ala | Glu | Phe |
| | | | 115 | | | | | 120 | | | | | 125 | | |
| Val | Asn | Asn | Thr | Thr | Gly | Glu | Ile | Lys | Ser | Gln | Thr | Val | Phe | Ile | Gly |
| | | 130 | | | | | 135 | | | | | 140 | | | |
| Asp | Phe | Pro | Met | Met | Thr | Asp | Lys | Gly | Thr | Phe | Ile | Ile | Asn | Gly | Thr |
| 145 | | | | | 150 | | | | | 155 | | | | | 160 |
| Glu | Arg | Val | Val | Val | Ser | Gln | Leu | Val | Arg | Ser | Pro | Gly | Val | Tyr | Phe |
| | | | | 165 | | | | | 170 | | | | | 175 | |
| Asp | Gln | Thr | Ile | Asp | Lys | Ser | Thr | Glu | Arg | Pro | Leu | His | Ala | Val | Lys |
| | | | 180 | | | | | 185 | | | | | 190 | | |
| Val | Ile | Pro | Ser | Arg | Gly | Ala | Trp | Leu | Glu | Phe | Asp | Val | Asp | Lys | Arg |
| | | 195 | | | | | 200 | | | | | 205 | | | |
| Asp | Ser | Val | Gly | Val | Arg | Ile | Asp | Arg | Lys | Arg | Gln | Pro | Val | Thr |
| | 210 | | | | | 215 | | | | | 220 | | | | |
| Val | Leu | Leu | Lys | Ala | Leu | Gly | Trp | Thr | Thr | Glu | Gln | Ile | Thr | Glu | Arg |
| 225 | | | | | 230 | | | | | 235 | | | | | 240 |
| Phe | Gly | Phe | Ser | Glu | Ile | Met | Met | Ser | Thr | Leu | Glu | Ser | Asp | Gly | Val |
| | | | | 245 | | | | | 250 | | | | | 255 | |
| Ala | Asn | Thr | Asp | Glu | Ala | Leu | Leu | Glu | Ile | Tyr | Arg | Lys | Gln | Arg | Pro |
| | | | 260 | | | | | 265 | | | | | 270 | | |
| Gly | Glu | Gln | Pro | Thr | Arg | Asp | Leu | Ala | Gln | Ser | Leu | Leu | Asp | Asn | Ser |
| | | | 275 | | | | | 280 | | | | | 285 | | |
| Phe | Phe | Arg | Ala | Lys | Arg | Tyr | Asp | Leu | Ala | Arg | Val | Gly | Arg | Tyr | Lys |
| | | 290 | | | | | 295 | | | | | 300 | | | |
| Ile | Asn | Arg | Lys | Leu | Gly | Leu | Gly | Gly | Asp | His | Asp | Gly | Leu | Met | Thr |
| 305 | | | | | 310 | | | | | 315 | | | | | 320 |
| Leu | Thr | Glu | Glu | Asp | Ile | Ala | Thr | Thr | Ile | Glu | Tyr | Leu | Val | Arg | Leu |
| | | | | 325 | | | | | 330 | | | | | 335 | |
| His | Ala | Gly | Glu | Arg | Val | Met | Thr | Ser | Pro | Asn | Gly | Glu | Glu | Ile | Pro |
| | | | 340 | | | | | 345 | | | | | 350 | | |
| Val | Glu | Thr | Asp | Asp | Ile | Asp | His | Phe | Gly | Asn | Arg | Arg | Leu | Arg | Thr |
| | | 355 | | | | | 360 | | | | | 365 | | | |
| Val | Gly | Glu | Leu | Ile | Gln | Asn | Gln | Val | Arg | Val | Gly | Leu | Ser | Arg | Met |
| | 370 | | | | | 375 | | | | | 380 | | | | |
| Glu | Arg | Val | Val | Arg | Glu | Arg | Met | Thr | Thr | Gln | Asp | Ala | Glu | Ser | Ile |
| 385 | | | | | 390 | | | | | 395 | | | | | 400 |

```
Thr Pro Thr Ser Leu Ile Asn Val Arg Pro Val Ser Ala Ala Ile Arg
            405                 410                 415

Glu Phe Phe Gly Thr Ser Gln Leu Ser Gln Phe Met Asp Gln Asn Asn
            420                 425                 430

Ser Leu Ser Gly Leu Thr Tyr Lys Arg Arg Leu Ser Ala Leu Gly Pro
            435                 440                 445

Gly Gly Leu Ser Arg Glu Arg Ala Gly Ile Glu Val Arg Asp Val His
        450                 455                 460

Pro Ser His Tyr Gly Arg Met Cys Pro Ile Glu Thr Pro Glu Gly Pro
465                 470                 475                 480

Asn Ile Gly Leu Ile Gly Ser Leu Ala Ser Tyr Ala Arg Val Asn Pro
                485                 490                 495

Phe Gly Phe Ile Glu Thr Pro Tyr Arg Arg Ile Ile Asp Gly Lys Leu
            500                 505                 510

Thr Asp Gln Ile Asp Tyr Leu Thr Ala Asp Glu Glu Asp Arg Phe Val
            515                 520                 525

Val Ala Gln Ala Asn Thr His Tyr Asp Glu Glu Gly Asn Ile Thr Asp
        530                 535                 540

Glu Thr Val Thr Val Arg Leu Lys Asp Gly Asp Ile Ala Met Val Gly
545                 550                 555                 560

Arg Asn Ala Val Asp Tyr Met Asp Val Ser Pro Arg Gln Met Val Ser
                565                 570                 575

Val Gly Thr Ala Met Ile Pro Phe Leu Glu His Asp Asp Ala Asn Arg
            580                 585                 590

Ala Leu Met Gly Ala Asn Met Gln Lys Gln Ala Val Pro Leu Ile Arg
        595                 600                 605

Ala Glu Ala Pro Phe Val Gly Thr Gly Met Glu Gln Arg Ala Ala Tyr
    610                 615                 620

Asp Ala Gly Asp Leu Val Ile Thr Pro Val Ala Gly Val Val Glu Asn
625                 630                 635                 640

Val Ser Ala Asp Phe Ile Thr Ile Met Ala Asp Asp Gly Lys Arg Glu
                645                 650                 655

Thr Tyr Leu Leu Arg Lys Phe Gln Arg Thr Asn Gln Gly Thr Ser Tyr
            660                 665                 670

Asn Gln Lys Pro Leu Val Asn Leu Gly Glu Arg Val Glu Ala Gly Gln
        675                 680                 685

Val Ile Ala Asp Gly Pro Gly Thr Phe Asn Gly Glu Met Ser Leu Gly
    690                 695                 700

Arg Asn Leu Leu Val Ala Phe Met Pro Trp Glu Gly His Asn Tyr Glu
705                 710                 715                 720

Asp Ala Ile Ile Leu Asn Gln Asn Ile Val Glu Gln Asp Ile Leu Thr
                725                 730                 735

Ser Ile His Ile Glu Glu His Glu Ile Asp Ala Arg Asp Thr Lys Leu
            740                 745                 750

Gly Ala Glu Glu Ile Thr Arg Asp Ile Pro Asn Val Ser Glu Glu Val
        755                 760                 765

Leu Lys Asp Leu Asp Asp Arg Gly Ile Val Arg Ile Gly Ala Asp Val
770                 775                 780

Arg Asp Gly Asp Ile Leu Val Gly Lys Val Thr Pro Lys Gly Glu Thr
785                 790                 795                 800

Glu Leu Thr Pro Glu Glu Arg Leu Leu Arg Ala Ile Phe Gly Glu Lys
            805                 810                 815

Ala Arg Glu Val Arg Asp Thr Ser Met Lys Val Pro His Gly Glu Thr
```

```
                    820                 825                 830
Gly Lys Val Ile Gly Val Arg His Phe Ser Arg Glu Asp Asp Asp
            835                 840                 845

Leu Ala Pro Gly Val Asn Glu Met Ile Arg Ile Tyr Val Ala Gln Lys
    850                 855                 860

Arg Lys Ile Gln Asp Gly Asp Lys Leu Ala Gly Arg His Gly Asn Lys
865                 870                 875                 880

Gly Val Val Gly Lys Ile Leu Pro Gln Glu Asp Met Pro Phe Leu Pro
                885                 890                 895

Asp Gly Thr Pro Val Asp Ile Ile Leu Asn Thr His Gly Val Pro Arg
            900                 905                 910

Arg Met Asn Ile Gly Gln Val Leu Glu Thr His Leu Gly Trp Leu Ala
            915                 920                 925

Ser Ala Gly Trp Ser Val Asp Pro Glu Asp Pro Glu Asn Ala Glu Leu
    930                 935                 940

Val Lys Thr Leu Pro Ala Asp Leu Leu Glu Val Pro Ala Gly Ser Leu
945                 950                 955                 960

Thr Ala Thr Pro Val Phe Asp Gly Ala Ser Asn Glu Glu Leu Ala Gly
                965                 970                 975

Leu Leu Ala Asn Ser Arg Pro Asn Arg Asp Gly Asp Val Met Val Asn
            980                 985                 990

Ala Asp Gly Lys Ala Thr Leu Ile Asp Gly Arg Ser Gly Glu Pro Tyr
    995                 1000                1005

Pro Tyr  Pro Val Ser Ile Gly  Tyr Met Tyr Met Leu  Lys Leu His
    1010                1015                1020

His Leu  Val Asp Glu Lys Ile  His Ala Arg Ser Thr  Gly Pro Tyr
    1025                1030                1035

Ser Met  Ile Thr Gln Gln Pro  Leu Gly Gly Lys Ala  Gln Phe Gly
    1040                1045                1050

Gly Gln  Arg Phe Gly Glu Met  Glu Val Trp Ala Met  Gln Ala Tyr
    1055                1060                1065

Gly Ala  Ala Tyr Thr Leu Gln  Glu Leu Leu Thr Ile  Lys Ser Asp
    1070                1075                1080

Asp Val  Val Gly Arg Val Lys  Val Tyr Glu Ala Ile  Val Lys Gly
    1085                1090                1095

Glu Asn  Ile Pro Asp Pro Gly  Ile Pro Glu Ser Phe  Lys Val Leu
    1100                1105                1110

Leu Lys  Glu Leu Gln Ser Leu  Cys Leu Asn Val Glu  Val Leu Ser
    1115                1120                1125

Ala Asp  Gly Thr Pro Met Glu  Leu Ala Gly Asp Asp  Asp Asp Phe
    1130                1135                1140

Asp Gln  Ala Gly Ala Ser Leu  Gly Ile Asn Leu Ser  Arg Asp Glu
    1145                1150                1155

Arg Ser  Asp Ala Asp Thr Ala
    1160                1165

<210> SEQ ID NO 7
<211> LENGTH: 1775
<212> TYPE: DNA
<213> ORGANISM: Corynebacterium glutamicum
<220> FEATURE:
<221> NAME/KEY: CDS
<222> LOCATION: (500)..(880)

<400> SEQUENCE: 7
```

-continued

```
cagctctaca agagtgtcta agtggcgggc attccatgct ttggaggagc gatcttcaaa      60
ttcctccaaa gtgagttgac ctcgggaaac agctgcagaa agttcatcca cgacttggtt     120
tcggttaagg tcagtggcga gcttctttgc tggttcgttt ccttgaggaa cagtcatggg     180
aaccattcta acaagggatt tggtgttttc tgcggctagc tgataatgtg aacggctgag     240
tcccactctt gtagttggga attgacggca cctcgcactc aagcgcggta tcgcccctgg     300
ttttccggga cgcggtggcg catgtttgca tttgatgagg ttgtccgtga catgtttggt     360
cgggccccaa aaagagcccc cttttttgcg tgtctggaca cttttttcaaa tccttcgcca    420 tcgacaagct cagccttcgt gttcgtcccc cgggcgtcac gtcagcagtt aaagaacaac     480
tccgaaataa ggatggttc atg cca act att cag cag ctg gtc cgt aag ggc      532
                     Met Pro Thr Ile Gln Gln Leu Val Arg Lys Gly
                      1               5                  10 cgc cac gat aag tcc gcc aag gtg gct acc gcg gca ctg aag ggt tcc       580
Arg His Asp Lys Ser Ala Lys Val Ala Thr Ala Ala Leu Lys Gly Ser
             15                  20                  25 cct cag cgt cgt ggc gta tgc acc cgt gtg tac acc acc acc cct aag       628
Pro Gln Arg Arg Gly Val Cys Thr Arg Val Tyr Thr Thr Thr Pro Lys
         30                  35                  40 aag cct aac tct gct ctt cgt aag gtc gct cgt gtg cgc ctt acc tcc       676
Lys Pro Asn Ser Ala Leu Arg Lys Val Ala Arg Val Arg Leu Thr Ser
     45                  50                  55 ggc atc gag gtt tcc gct tac atc cct ggt gag ggc cac aac ctg cag       724
Gly Ile Glu Val Ser Ala Tyr Ile Pro Gly Glu Gly His Asn Leu Gln
 60                  65                  70                  75 gag cac tcc atg gtg ctc gtt cgc ggt ggt cgt gtt aag gac ctc cca       772
Glu His Ser Met Val Leu Val Arg Gly Gly Arg Val Lys Asp Leu Pro
                 80                  85                  90 ggt gtc cgt tac aag atc gtc cgt ggc gca ctg gat acc cag ggt gtt       820
Gly Val Arg Tyr Lys Ile Val Arg Gly Ala Leu Asp Thr Gln Gly Val
             95                 100                 105 aag gac cgc aag cag gct cgt tcc ccg cta cgg cgc gaa gag ggg ata       868
Lys Asp Arg Lys Gln Ala Arg Ser Pro Leu Arg Arg Glu Glu Gly Ile
        110                 115                 120 att aaa aat gcg taaatcagca gctcctaagc gtccagtagt tcaggaccct           920
Ile Lys Asn Ala
        125 gtatacaagt ccgagctcgt tacccagctc gtaaacaaga tcctcatcgg tggcaagaag     980 tccaccgcag agcgcatcgt ctacggtgca ctcgagatct gccgtgagaa gaccggcacc    1040 gatccagtag gaaccctcga gaaggctctc ggcaacgtgc gtccagacct cgaagttcgt    1100 tcccgccgtg ttggtggcgc tacctaccag gtgccagtgg atgttcgccc agagcgcgca    1160 aacaccctcg cactgcgttg gttggtaacc ttcacccgtc agcgtcgtga aacaccatg     1220 atcgagcgtc ttgcaaacga acttctggat gcagccaacg gccttggcgc ttccgtgaag    1280 cgtcgcgaag acacccacaa gatggcagag gccaaccgcg ccttcgctca ctaccgctgg    1340 tagtactgcc aagacatgaa agcccaatca cctttaagat caacgcctgc cggcgccctt    1400 cacatttgaa taagctggca gcctgcgttt cttcaaggcg actgggcttt tagtctcatt    1460 aatgcagttc accgctgtaa gatagctaaa tagaaacact gtttcggcag tgtgttacta    1520 aaaaatccat gtcacttgcc tcgagcgtgc tgcttgaatc gcaagttagt ggcaaaatgt    1580 aacaagagaa ttatccgtag gtgacaaact ttttaatact tgggtatctg tcatggatac    1640 cccggtaata aataagtgaa ttaccgtaac caacaagttg gggtaccact gtggcacaag    1700 aagtgcttaa ggatctaaac aaggtccgca acatcggcat catggcgcac atcgatgctg    1760
```

```
-continued gtaagaccac gacca                                                        1775

<210> SEQ ID NO 8
<211> LENGTH: 127
<212> TYPE: PRT
<213> ORGANISM: Corynebacterium glutamicum

<400> SEQUENCE: 8

Met Pro Thr Ile Gln Gln Leu Val Arg Lys Gly Arg His Asp Lys Ser
1               5                   10                  15

Ala Lys Val Ala Thr Ala Ala Leu Lys Gly Ser Pro Gln Arg Arg Gly
                20                  25                  30

Val Cys Thr Arg Val Tyr Thr Thr Pro Lys Lys Pro Asn Ser Ala
            35                  40                  45

Leu Arg Lys Val Ala Arg Val Arg Leu Thr Ser Gly Ile Glu Val Ser
    50                  55                  60

Ala Tyr Ile Pro Gly Glu Gly His Asn Leu Gln Glu His Ser Met Val
65                  70                  75                  80

Leu Val Arg Gly Gly Arg Val Lys Asp Leu Pro Gly Val Arg Tyr Lys
                85                  90                  95

Ile Val Arg Gly Ala Leu Asp Thr Gln Gly Val Lys Asp Arg Lys Gln
                100                 105                 110

Ala Arg Ser Pro Leu Arg Arg Glu Glu Gly Ile Ile Lys Asn Ala
            115                 120                 125
```